United States Patent [19]

Pardue et al.

[11] Patent Number: 5,018,577
[45] Date of Patent: May 28, 1991

[54] PHOSPHINATE INHIBITOR FOR SCALE SQUEEZE APPLICATIONS

[75] Inventors: Jerry E. Pardue, Sugarland, Tex.; James F. Kneller, LaGrange Park, Ill.

[73] Assignee: Nalco Chemical Company, Naperville, Ill.

[21] Appl. No.: 561,854

[22] Filed: Aug. 2, 1990

[51] Int. Cl.$^5$ .................. C02F 5/14; E21B 37/00; E21B 43/22
[52] U.S. Cl. ................. 166/279; 166/263; 166/312; 210/699; 252/8.552
[58] Field of Search ............. 166/263, 270, 273, 274, 166/279, 300, 305.1, 312, 371; 252/8.552; 210/699

[56] References Cited

U.S. PATENT DOCUMENTS

| | | | |
|---|---|---|---|
| 3,483,925 | 12/1969 | Slyker | 166/279 |
| 3,502,587 | 3/1970 | Stanford et al. | 252/8.552 X |
| 4,088,678 | 5/1978 | Matt et al. | 210/700 X |
| 4,297,237 | 10/1981 | Boffardi | 252/8.552 X |
| 4,393,935 | 7/1983 | Walton | 252/8.552 X |
| 4,563,284 | 1/1986 | Amjad | 252/8.552 X |
| 4,660,645 | 4/1987 | Newlove et al. | 166/312 X |
| 4,663,053 | 5/1987 | Geiger | 210/699 |
| 4,913,823 | 4/1990 | Lipinski et al. | 210/699 |

Primary Examiner—George A. Suchfield
Attorney, Agent, or Firm—John G. Premo; Robert A. Miller

[57] ABSTRACT

A squeeze treatment for preventing scale utilizes as the scale inhibitor a predominantly phosphinate containing composition comprising:

| Ingredients | Mole Percent - Less Than |
|---|---|
| A. Monosodium phosphinicobis - (succinic acid) | 22 |
| B. Monosodium phosphinico-succinic acid | 26 |
| C. Sodium phosphonosuccinic acid | 12 |
| D. Sodium phosphate | 5 |
| E. Sodium phosphite | 6 |
| F. Sodium hypophosphite, and | 6 |
| G. A phosphinicosuccinic acid oligomer having the probable structural formula: | |

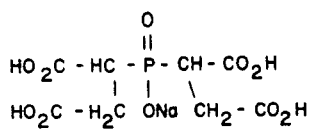

wherein G exceeds 25 mole percent, M is H, Na, K, NH$_4$, amine salts and mixtures thereof and m and n are either 0 or a small whole number with the proviso that either m or n is a small whole number and the sum of m plus n is greater than 2.

8 Claims, 25 Drawing Sheets

Components of the Maleic Acid
Sodium Hypophosphite Reaction $$HO_2C - HC - \overset{\overset{O}{\|}}{P} - CH - CO_2H$$
$$HO_2C - H_2C \quad ONa \quad CH_2 - CO_2H$$

Monosodium Phosphinicobis
bis (succinic) Acid
"2:1"

Phosphinicosuccinic
Acid
"1:1"

Phosphonosuccinic
Acid
"PSA"

Oligomer

Phosphate

Phosphite

Hypophosphite

FIG. I
Components of the Maleic Acid Sodium Hypophosphite Reaction
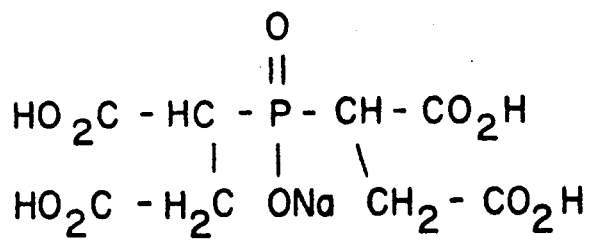
Monosodium Phosphinicobis
bis(succinic) Acid
"2:1"
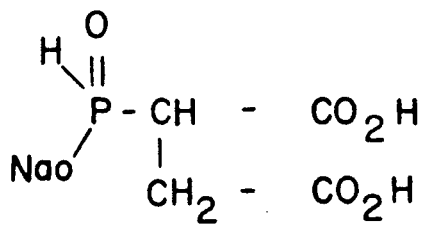
Phosphinicosuccinic
Acid
"1:1"
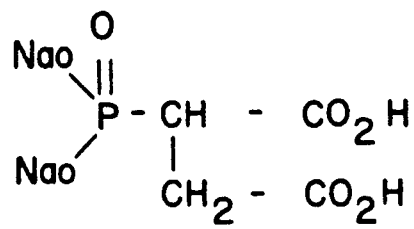
Phosphonosuccinic
Acid
"PSA"
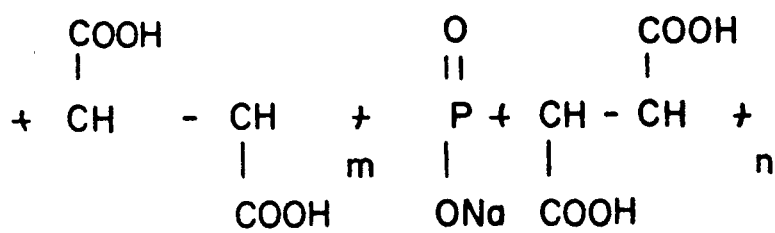
Oligomer
$Na_3PO_4$     $Na_2HPO_3$     $NaH_2PO_2$
Phosphate     Phosphite     Hypophosphite

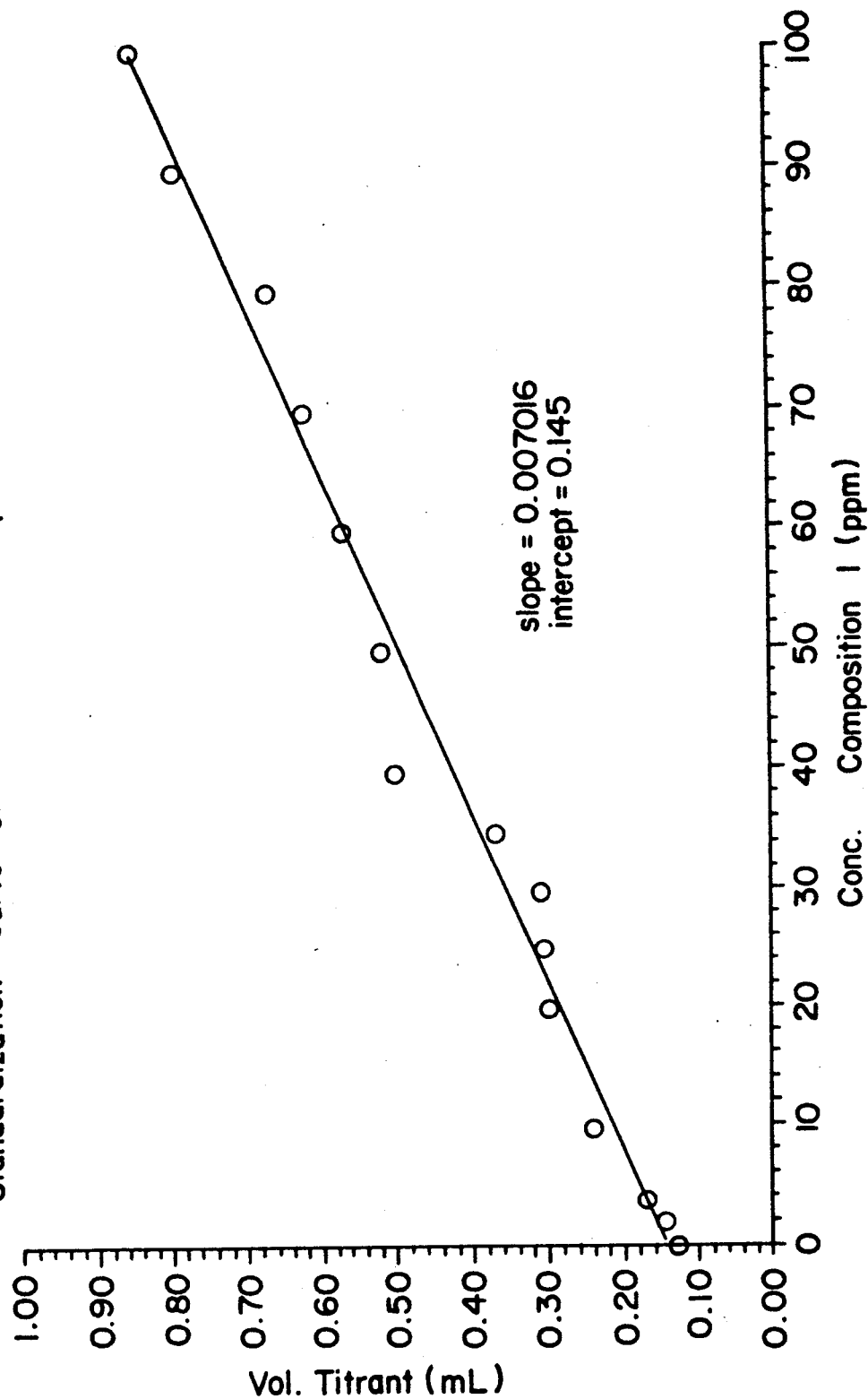

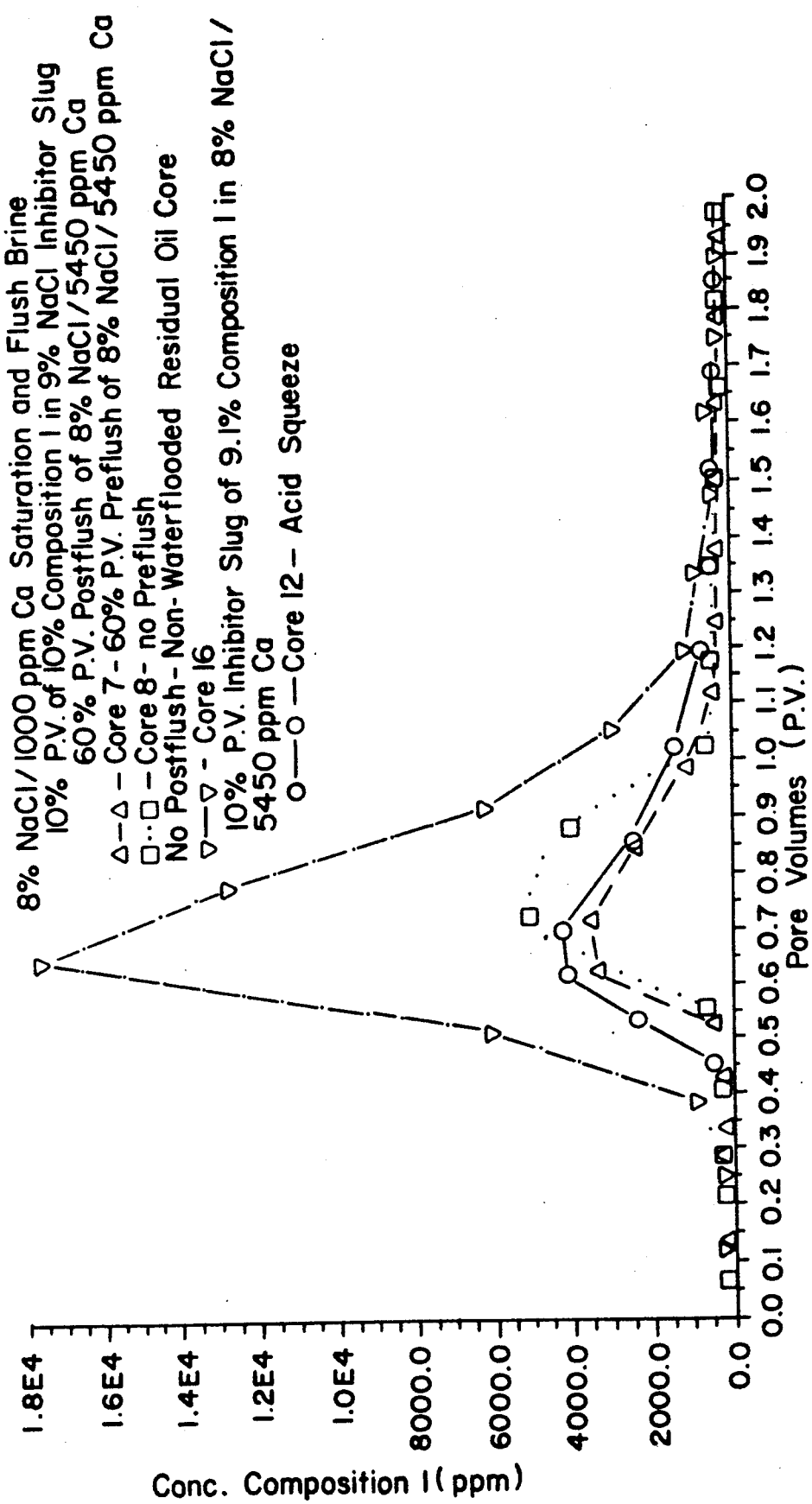

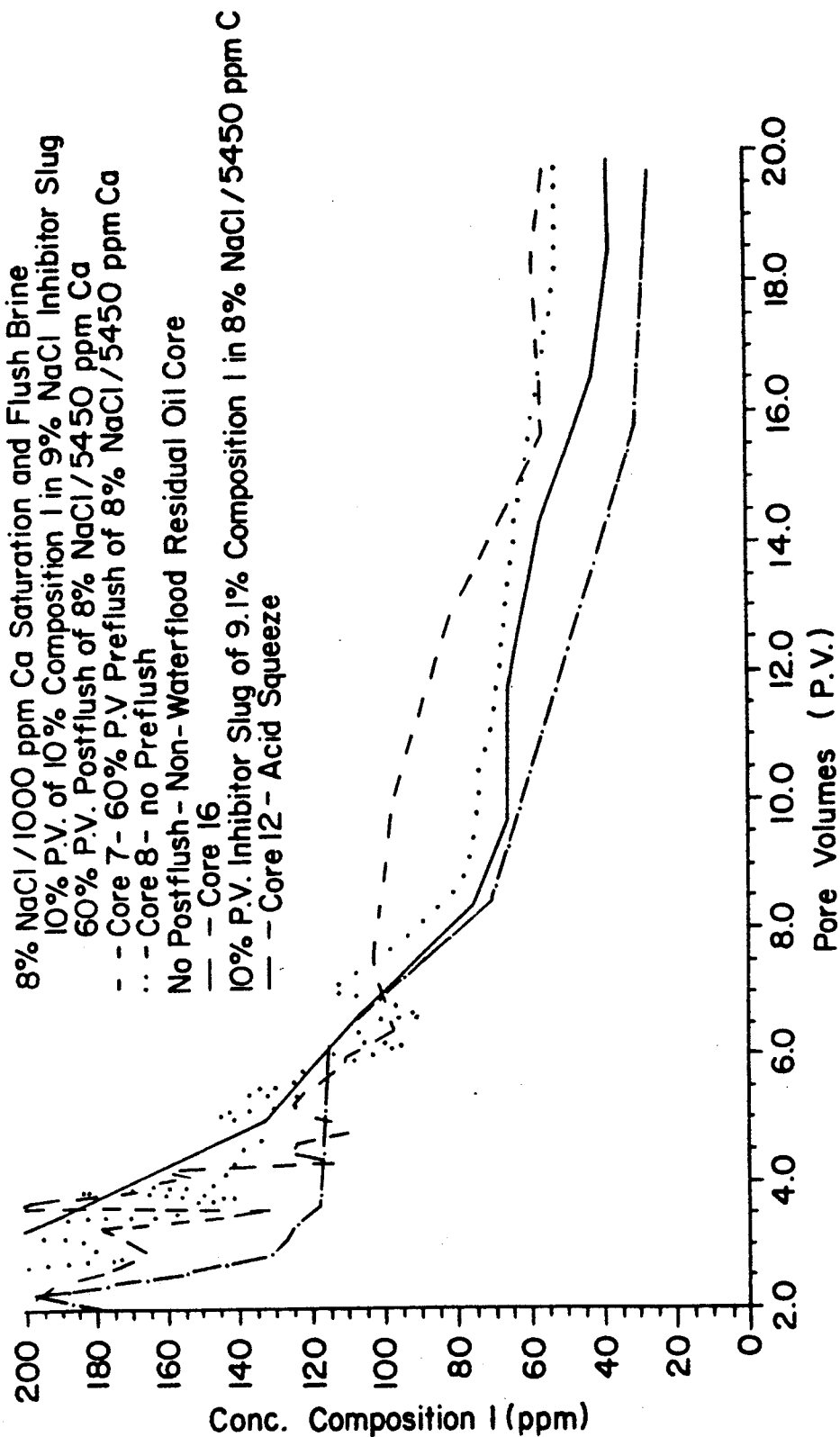

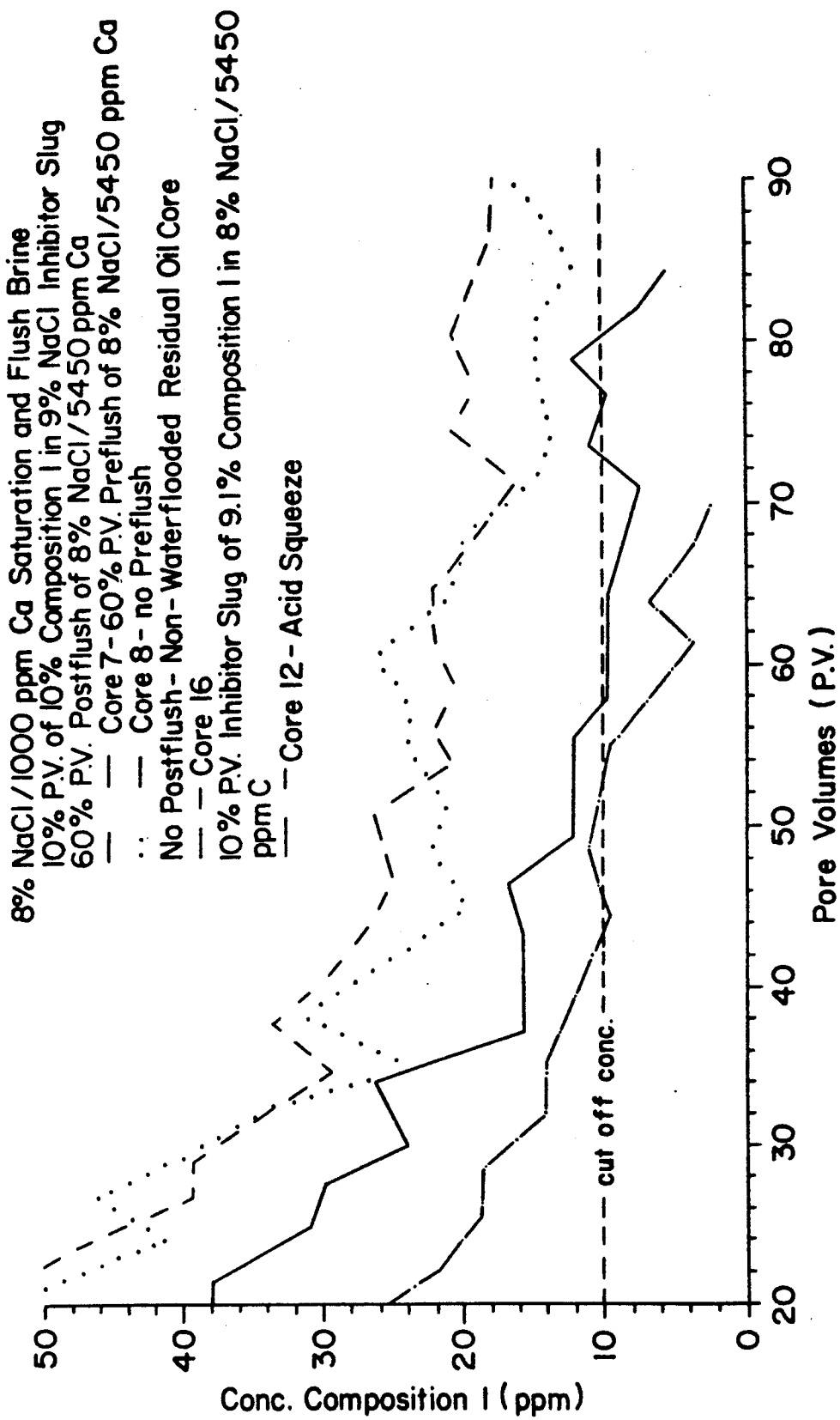

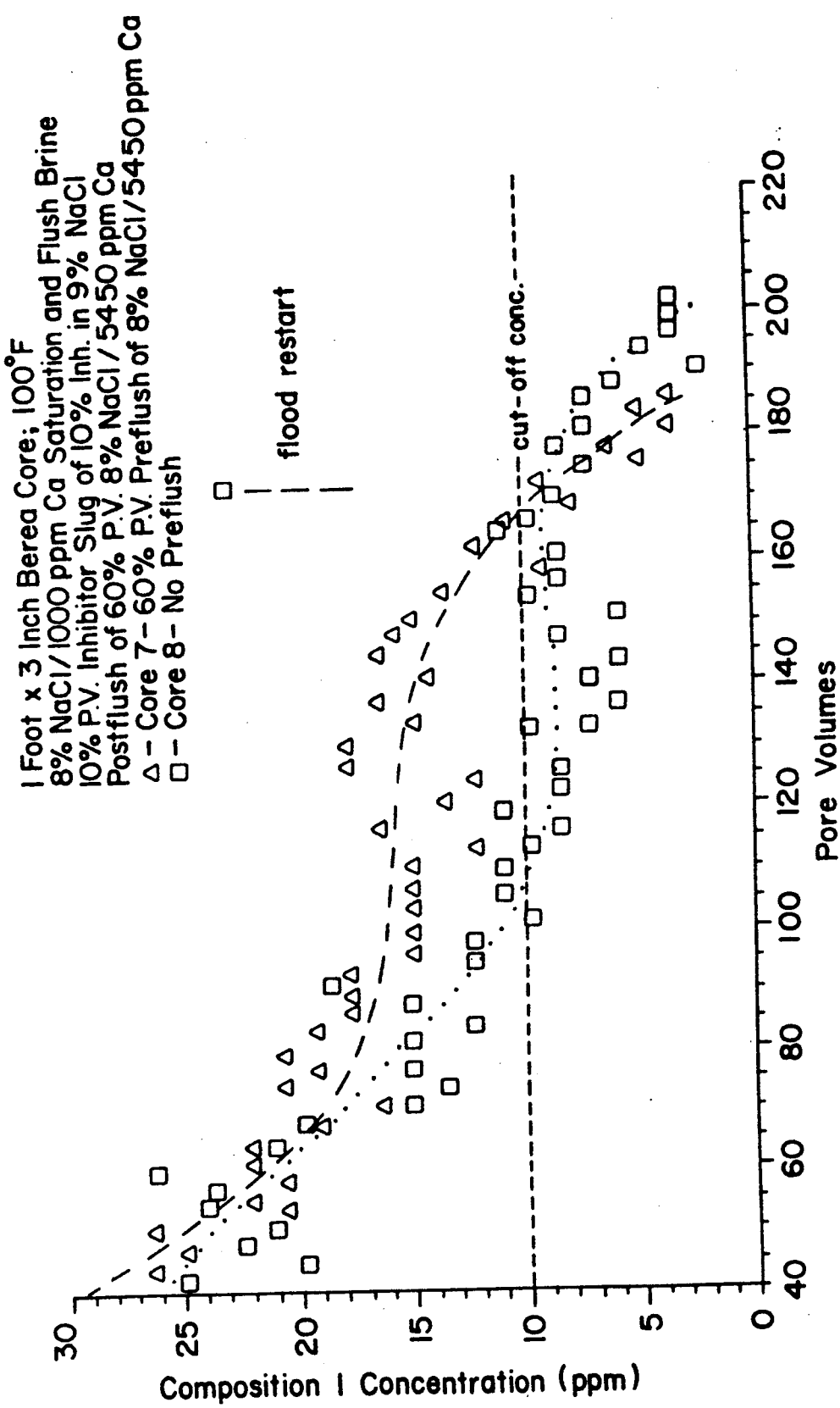

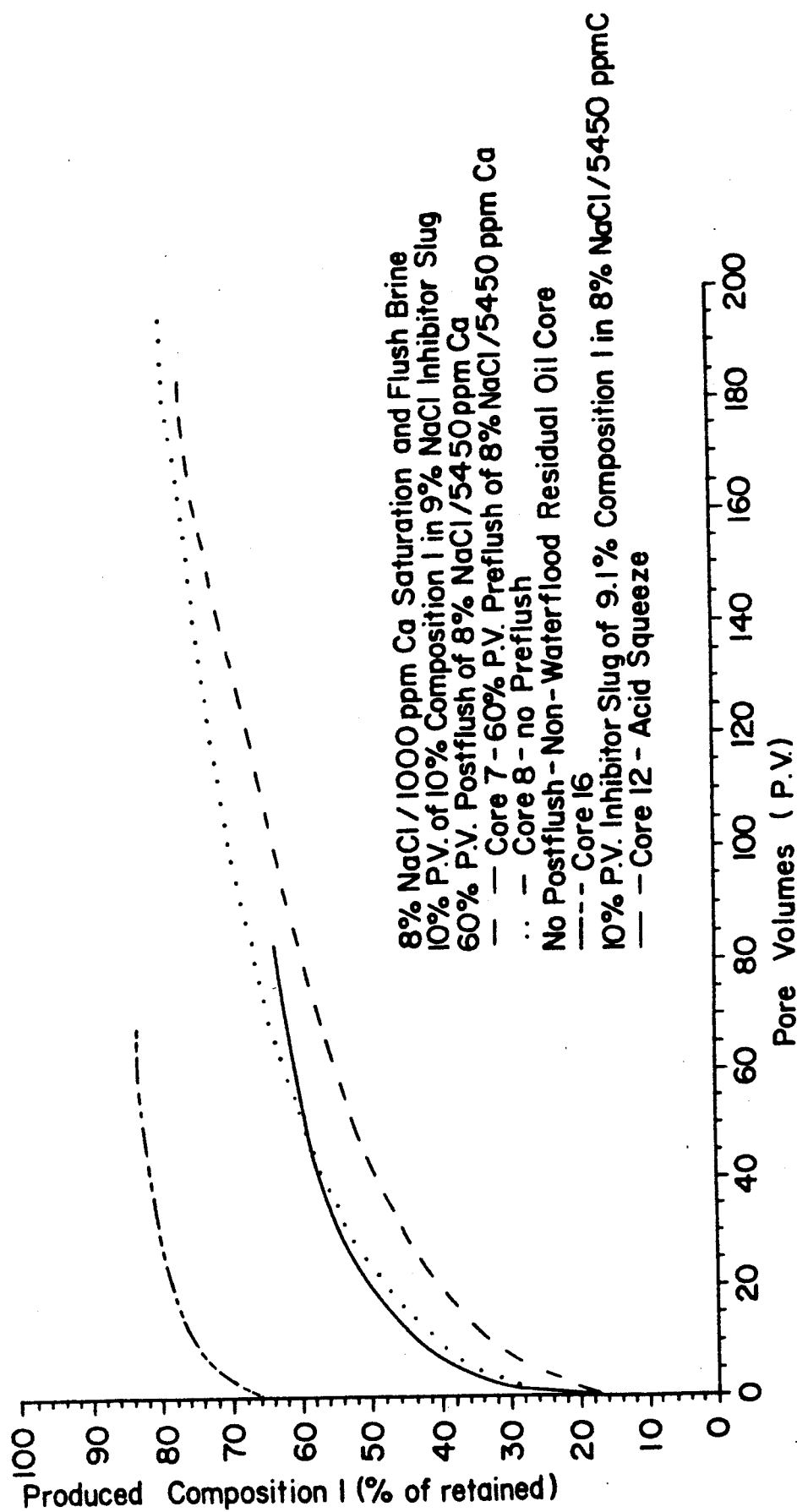

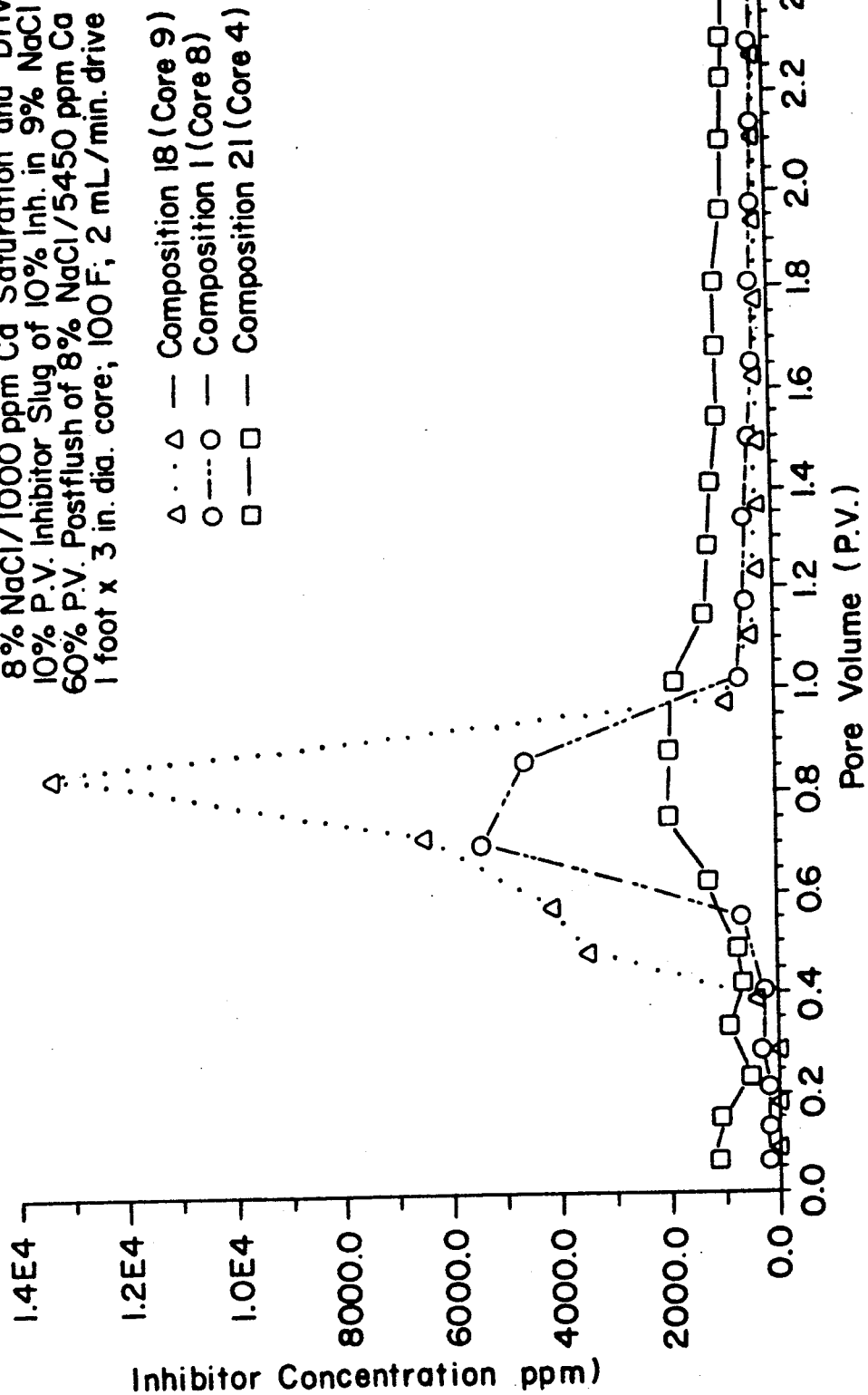

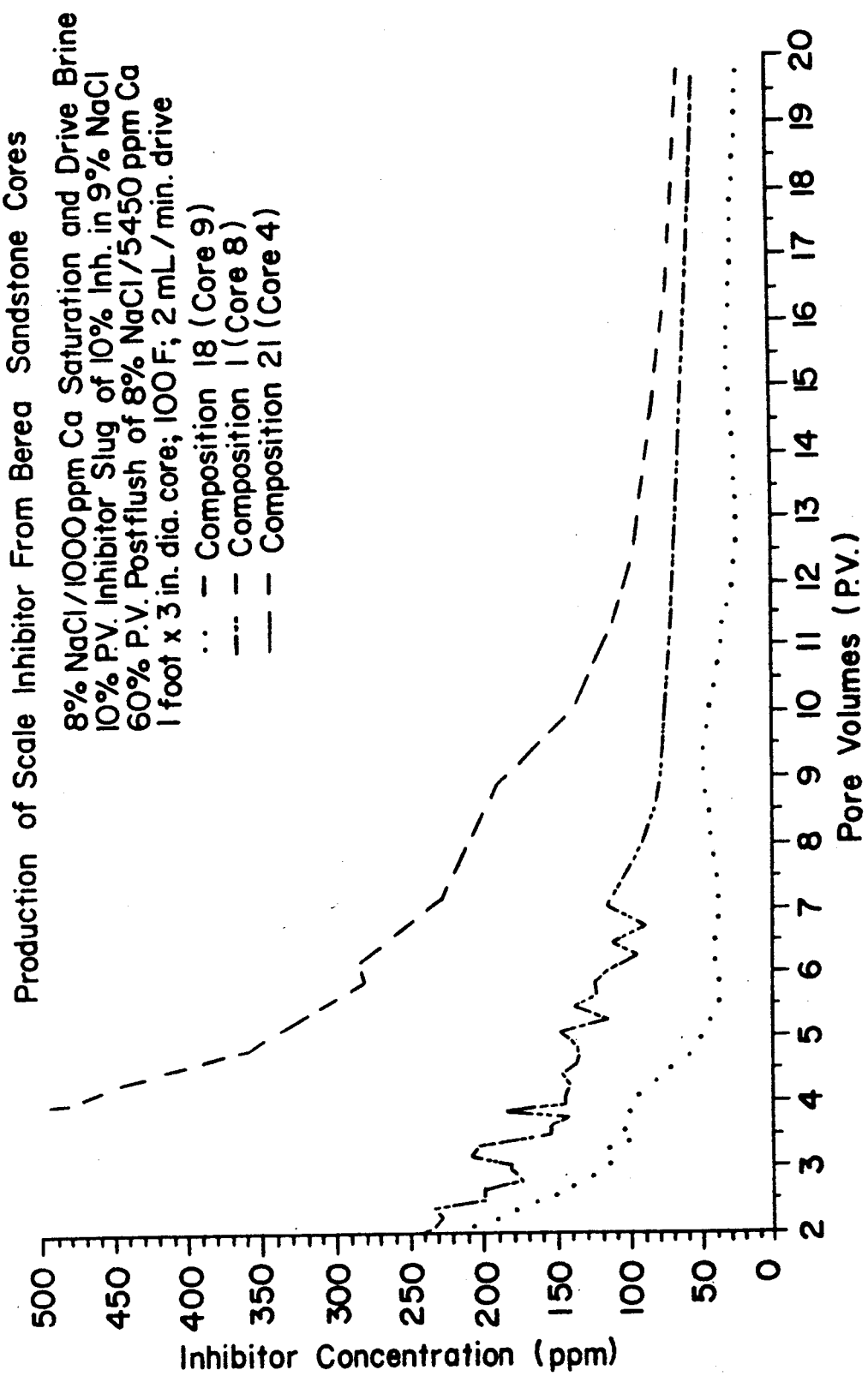

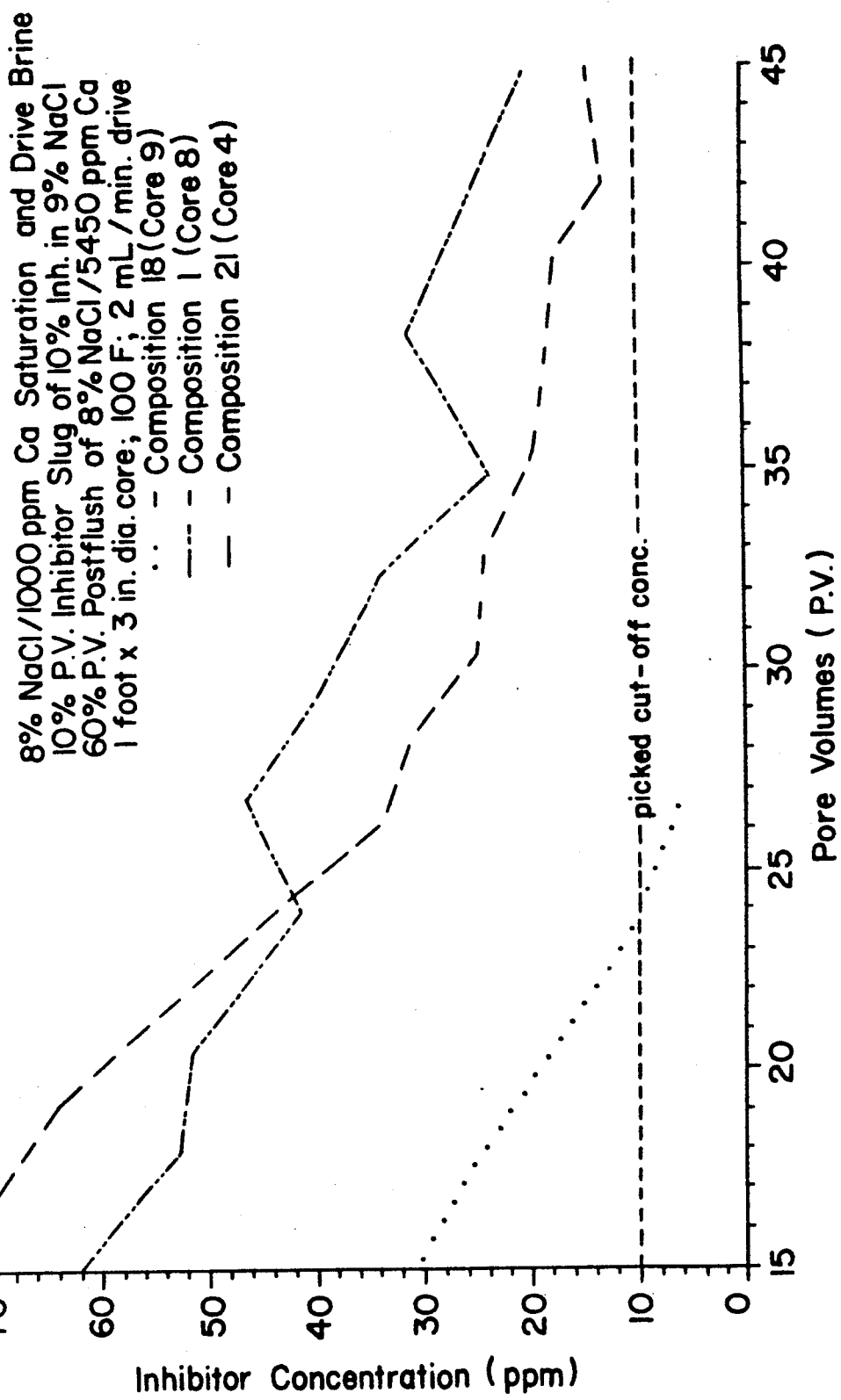

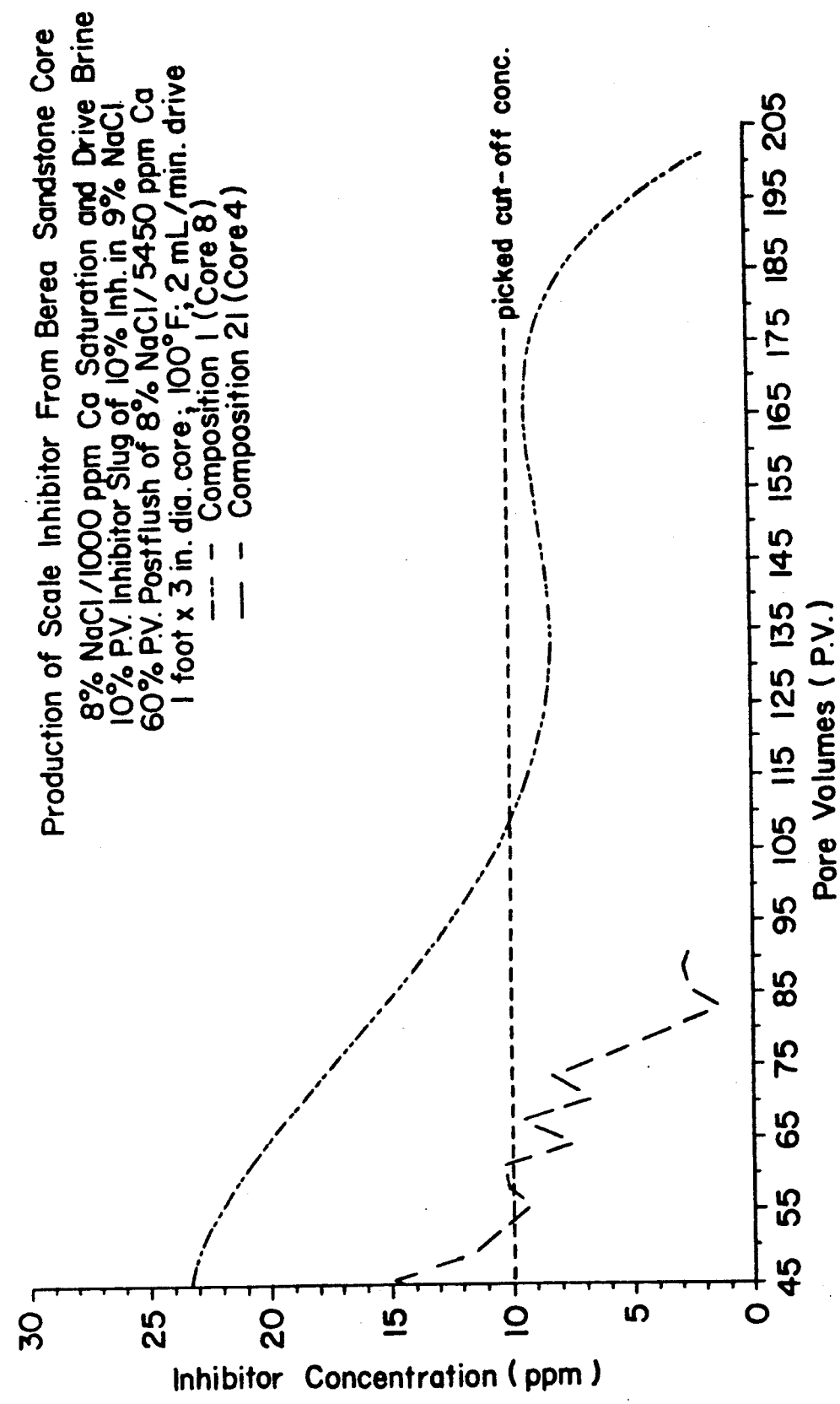

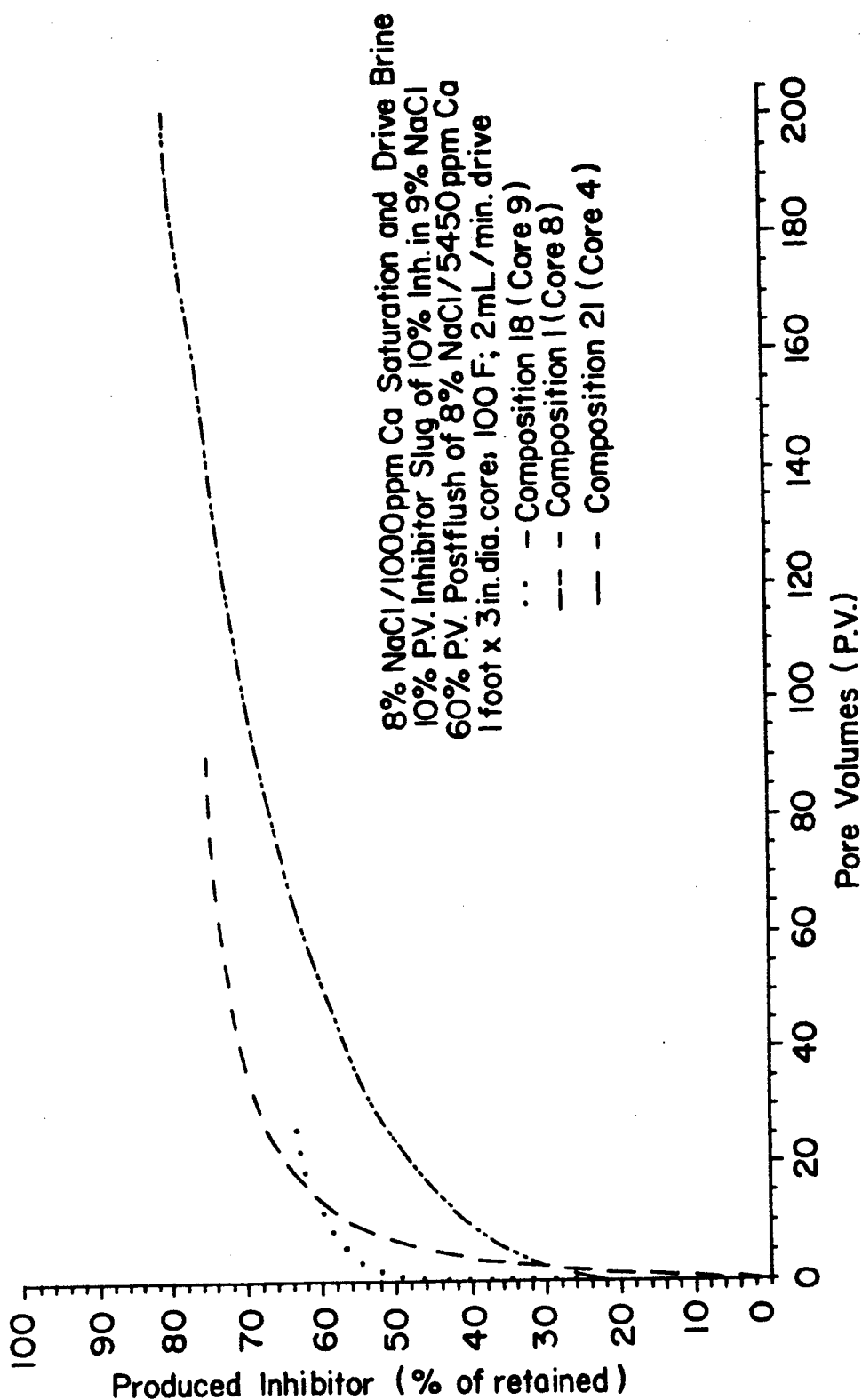

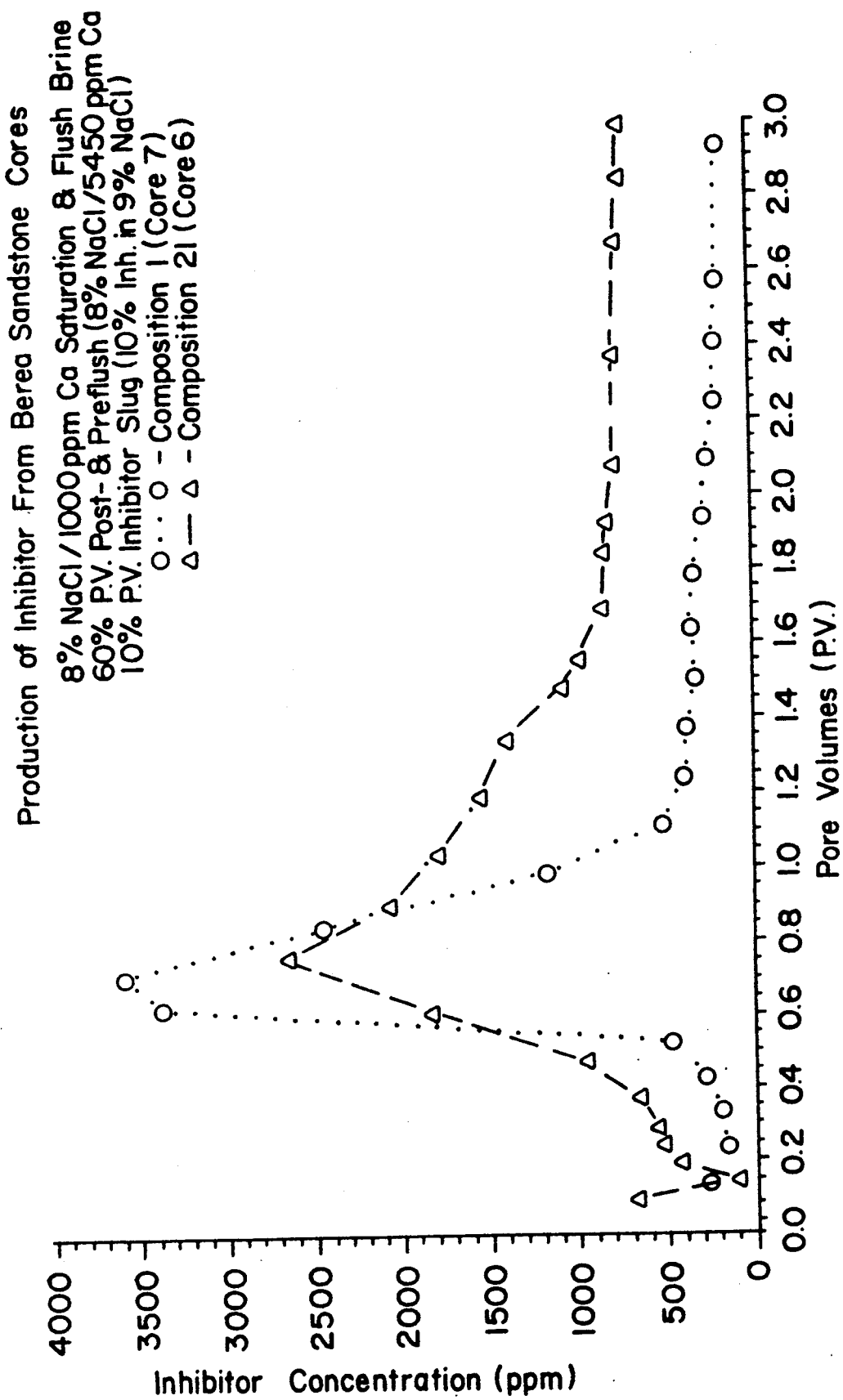

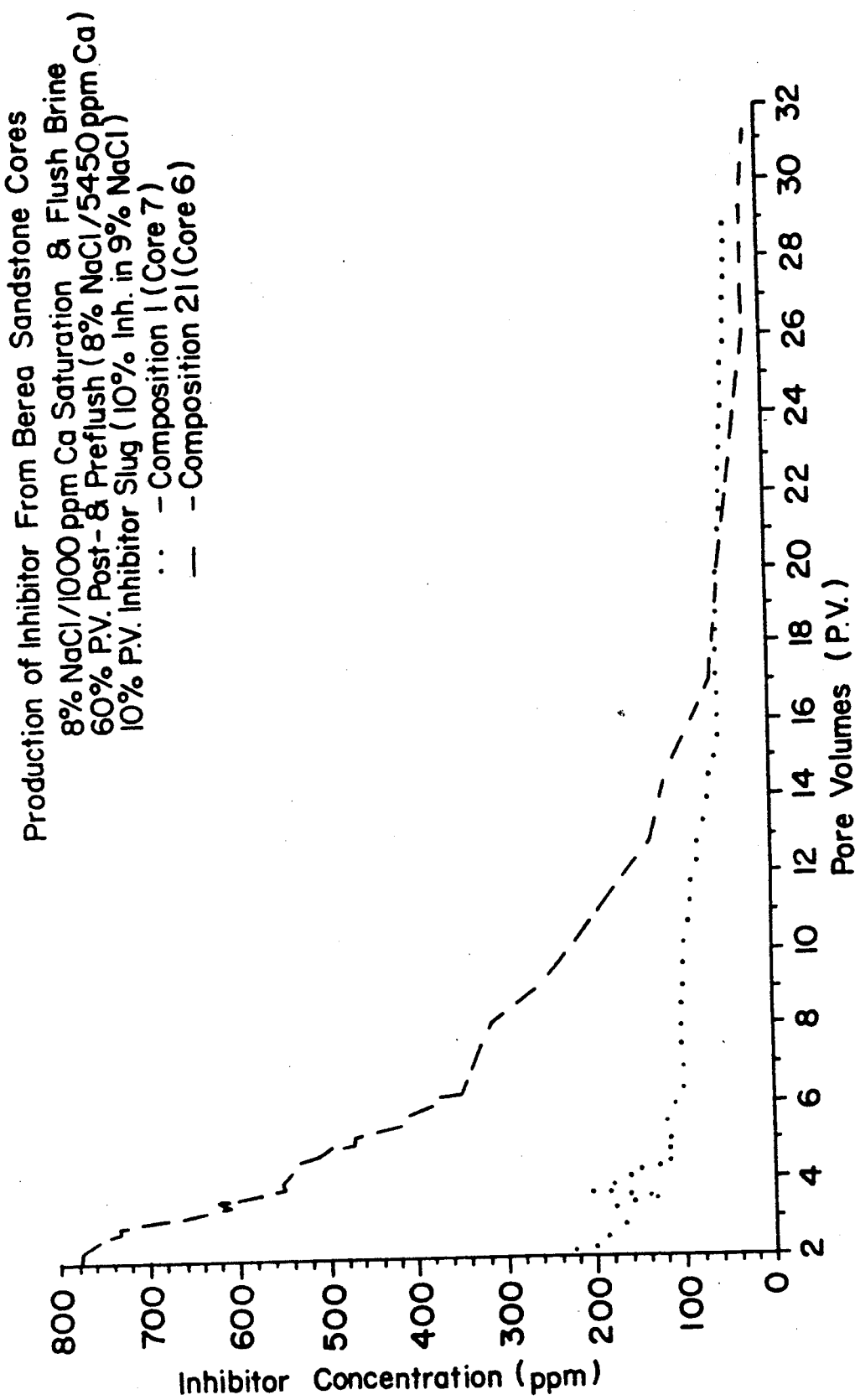

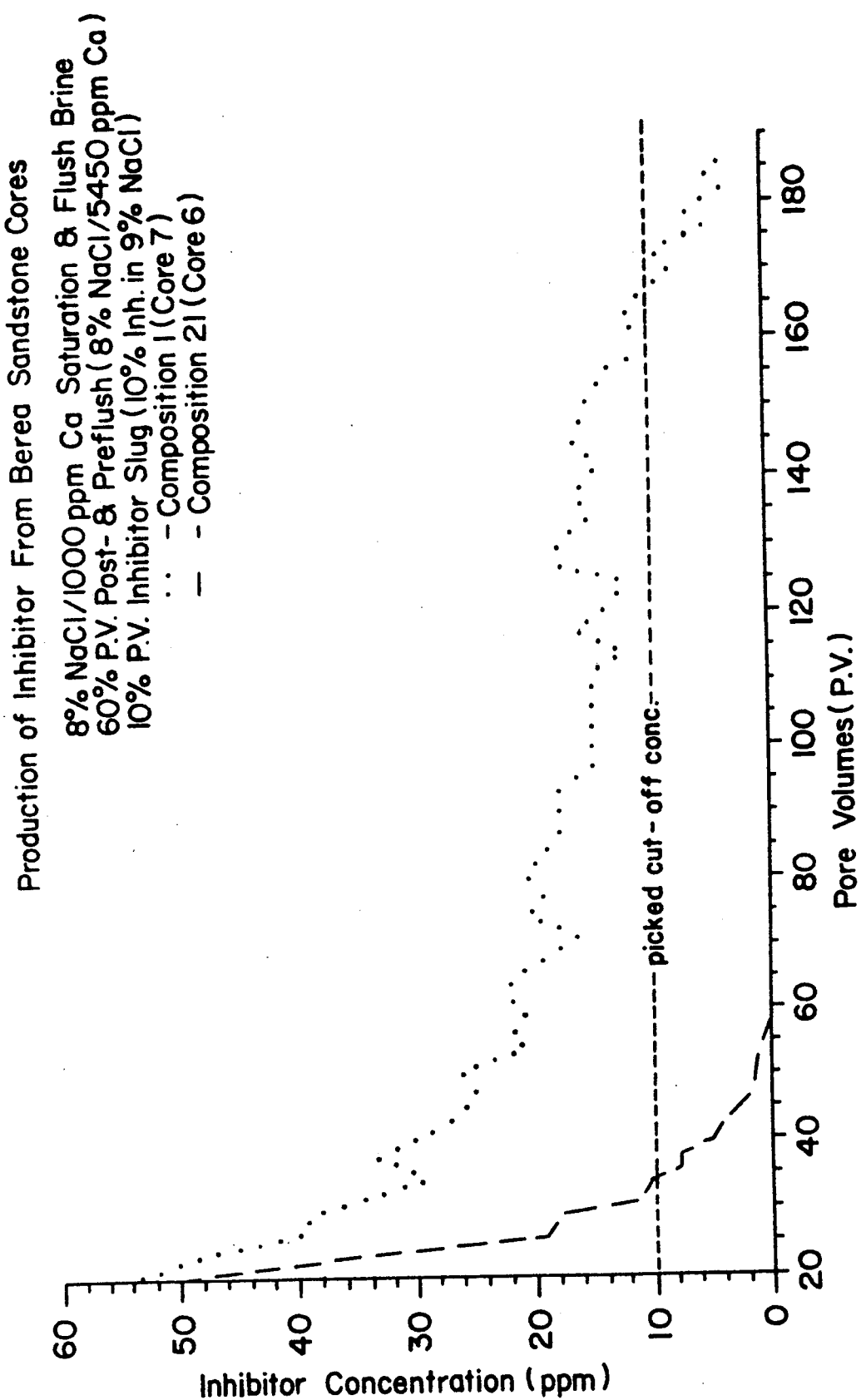

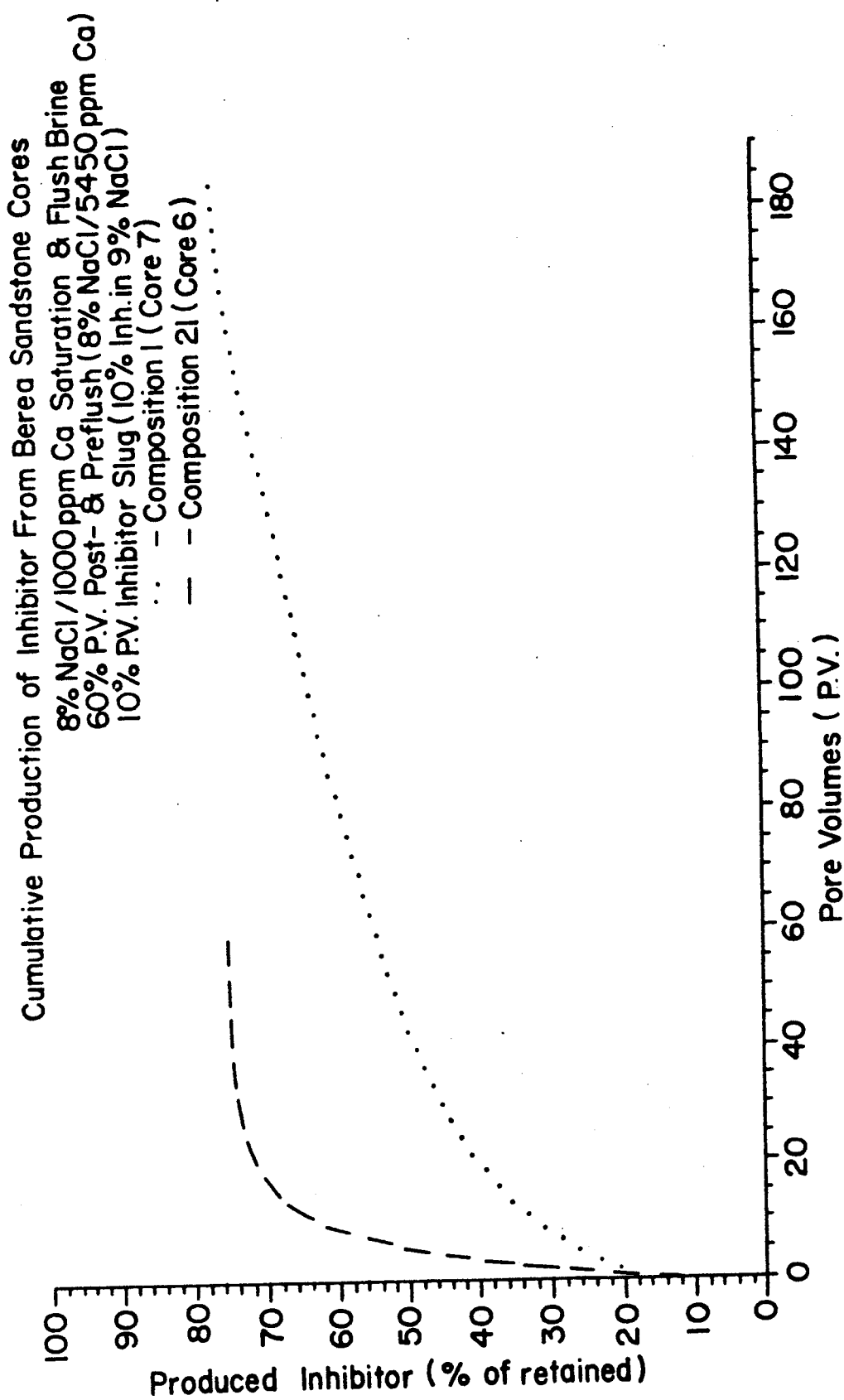

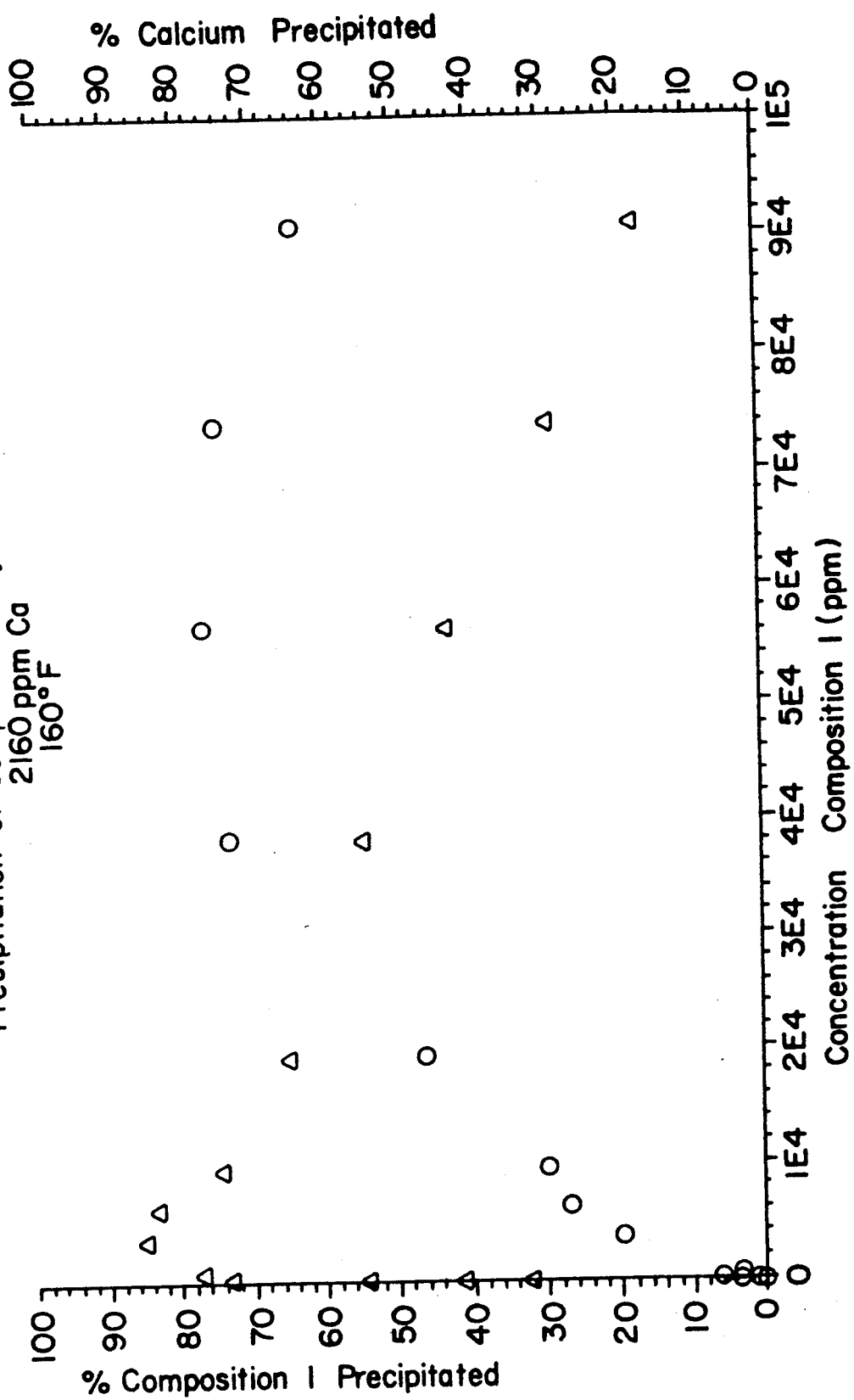

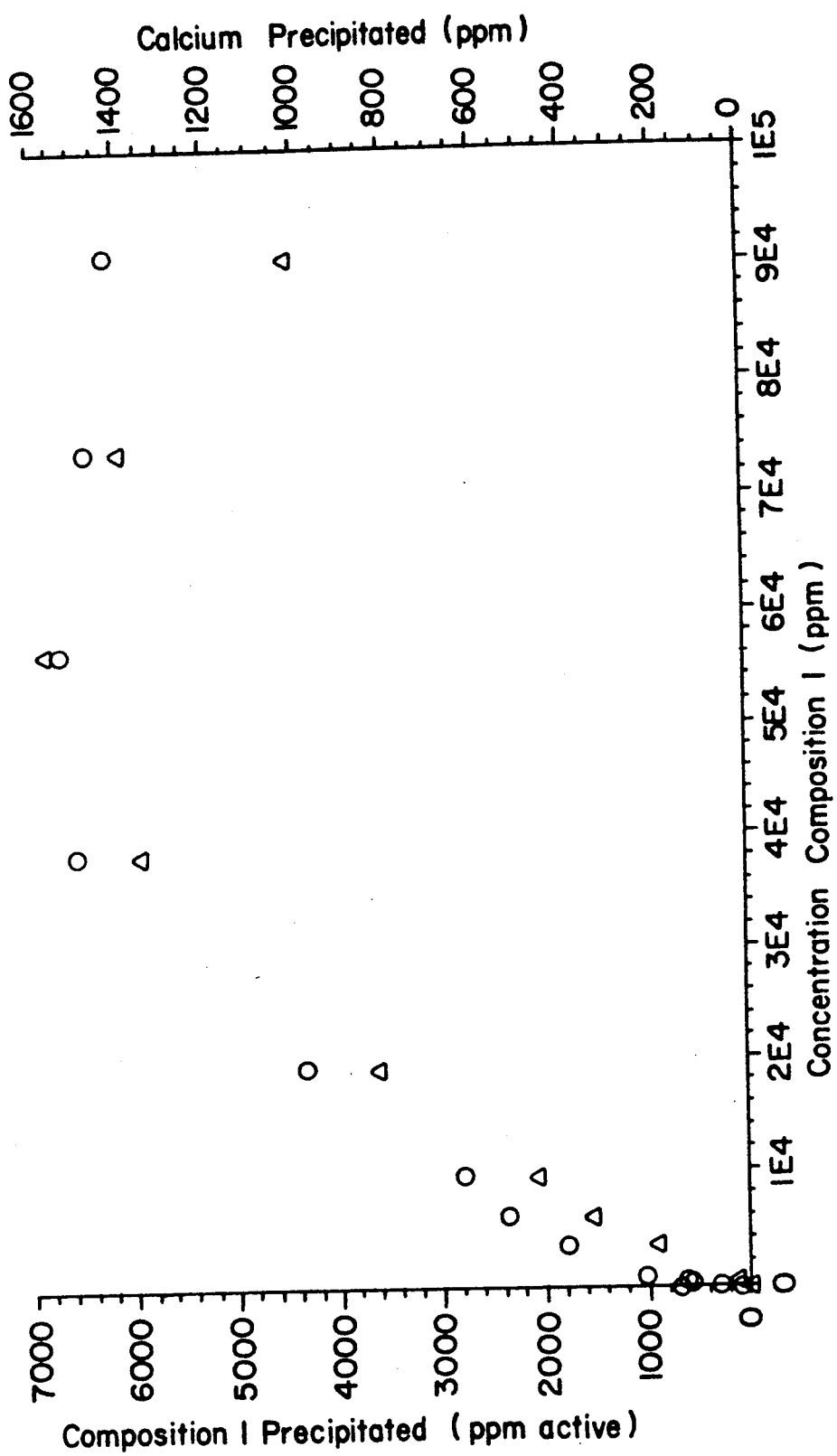

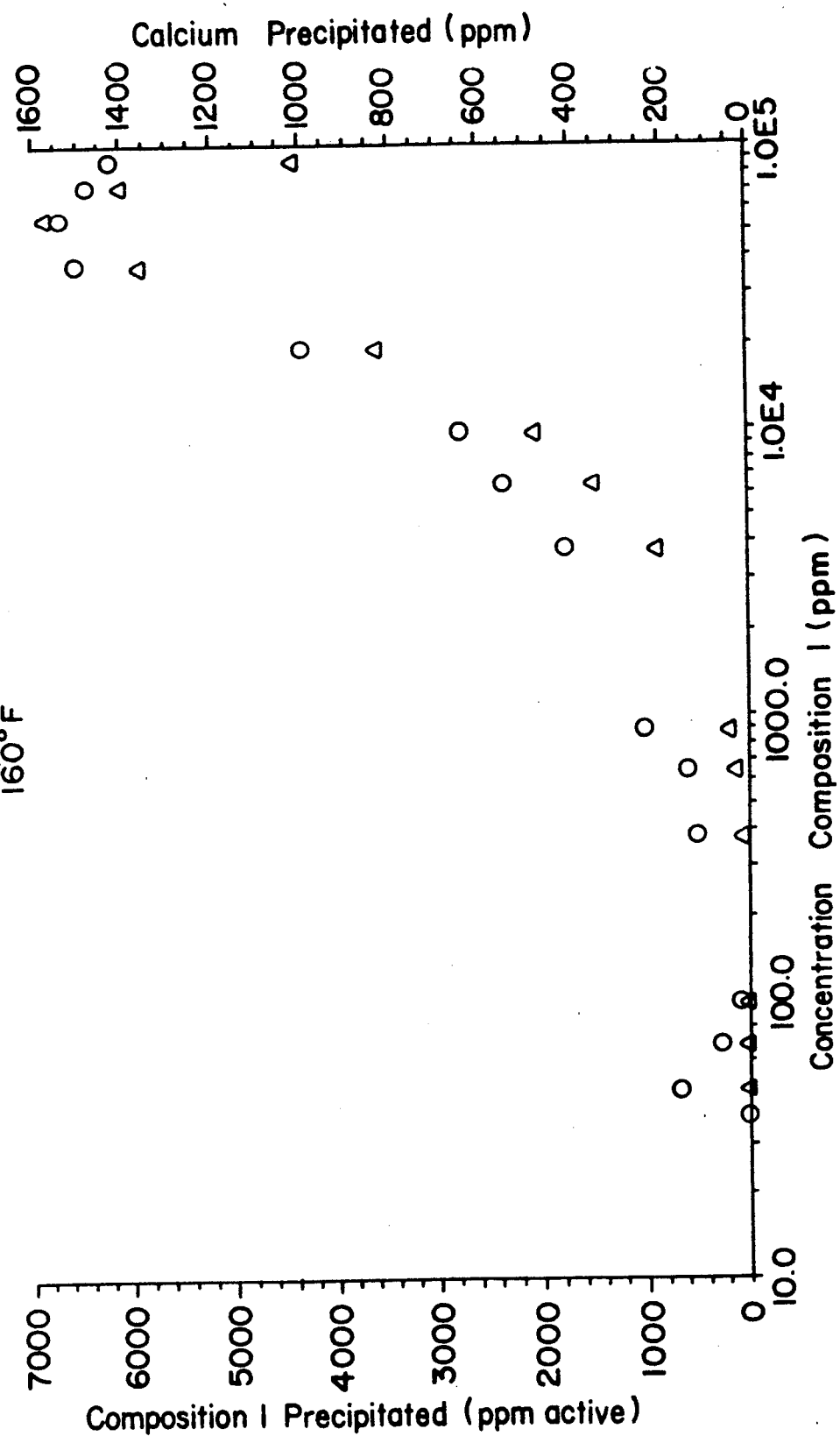
FIG. 19 Precipitation of Composition I by Field Brine 2160 ppm Ca 160°F

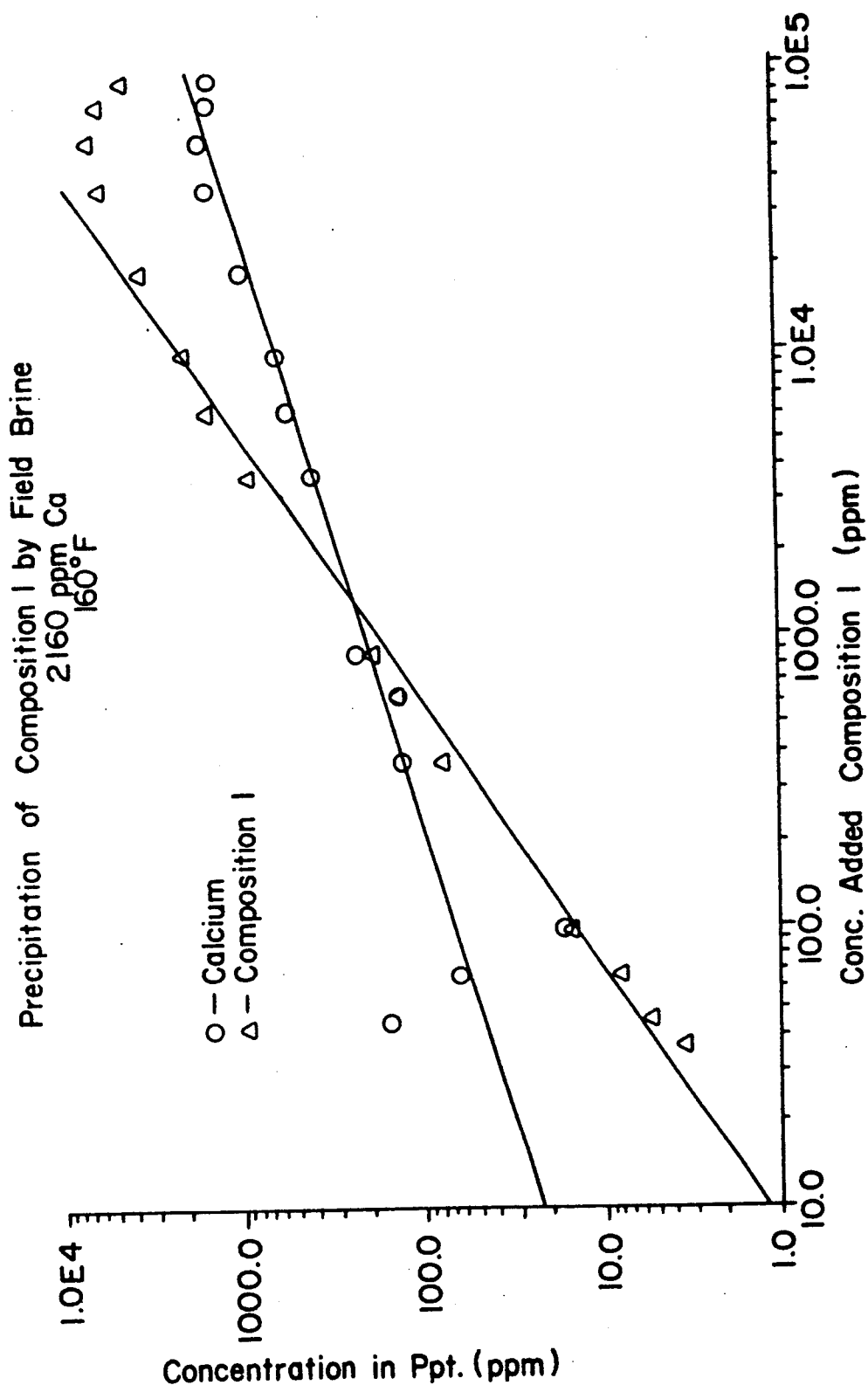

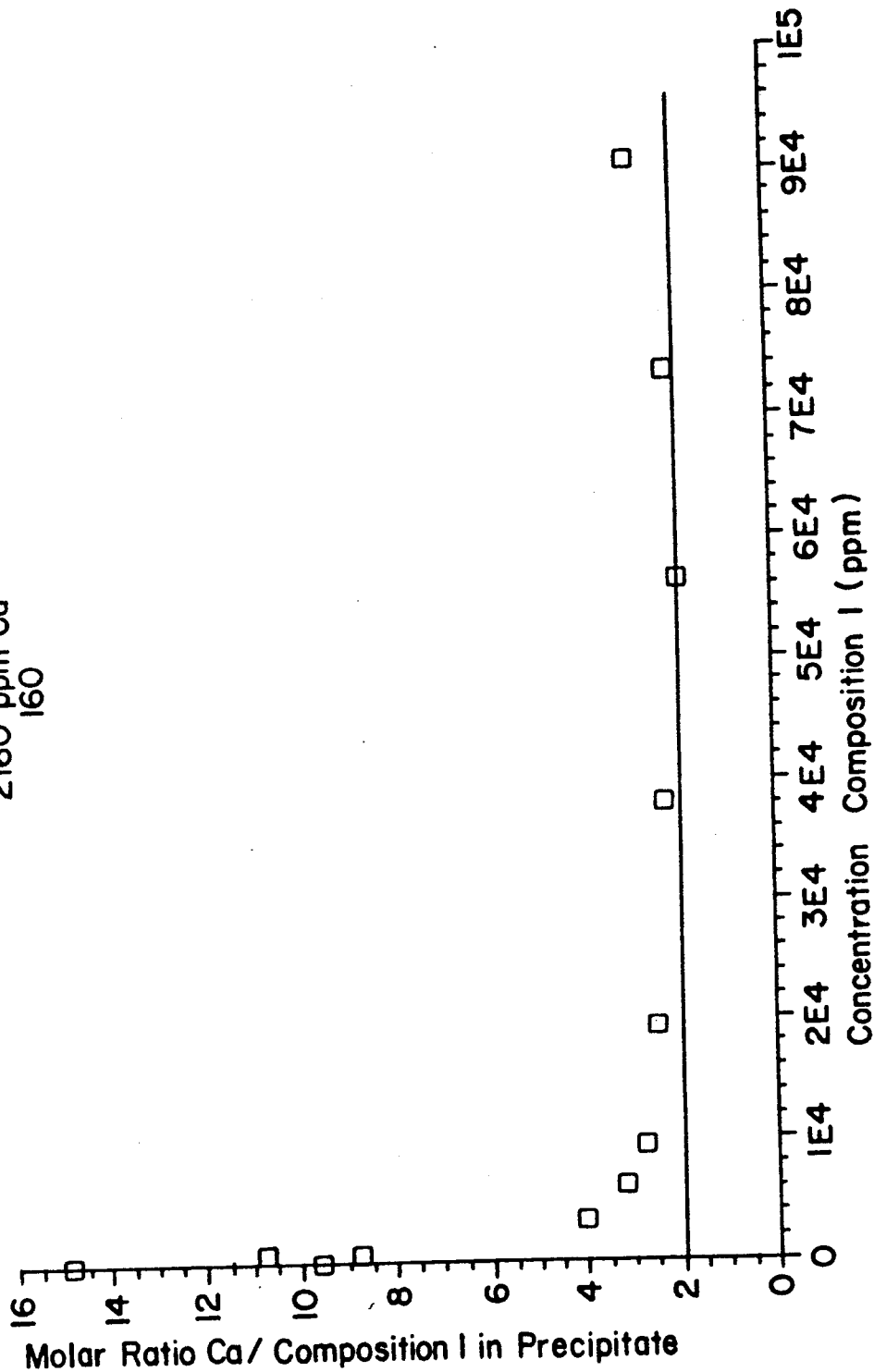

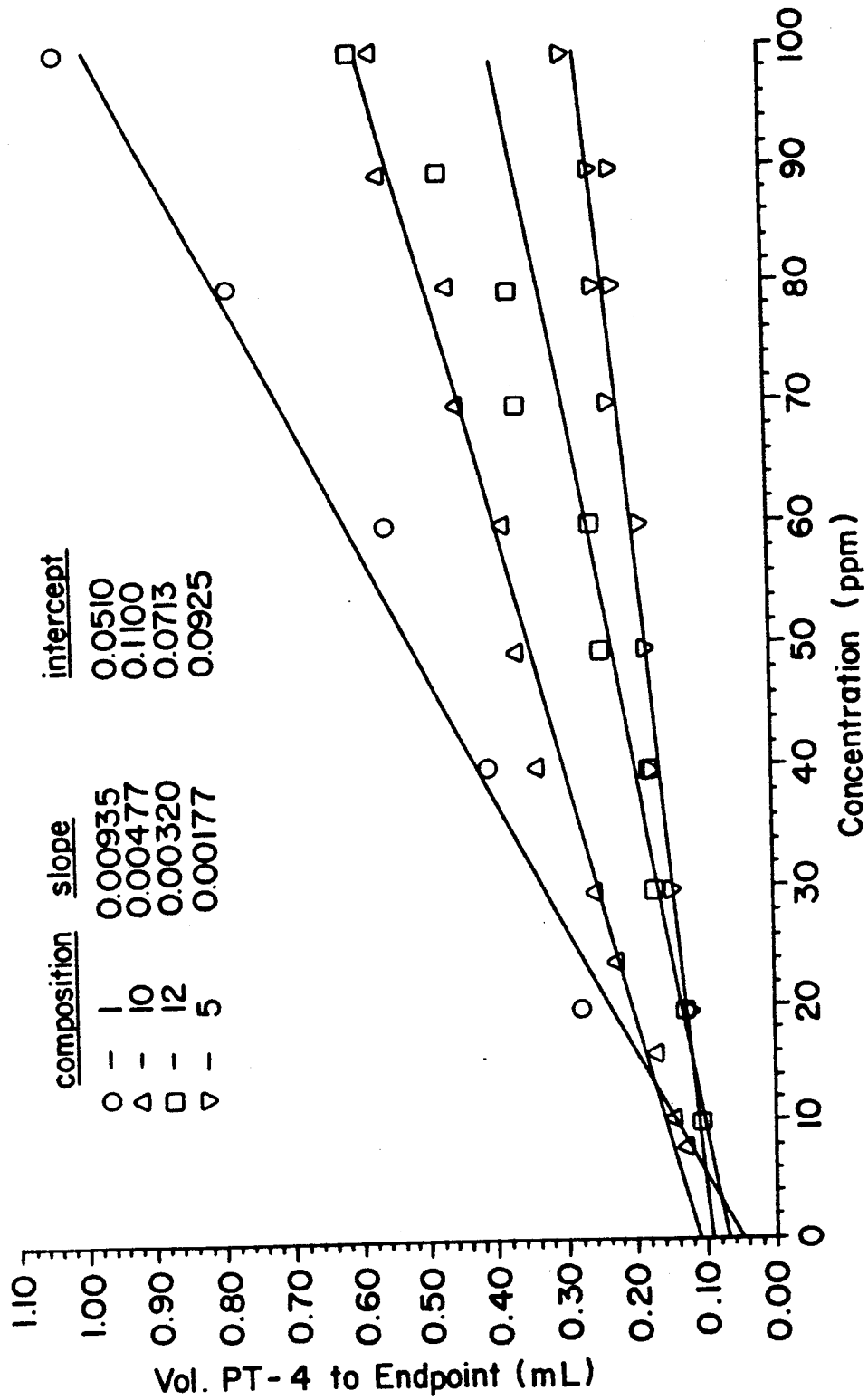

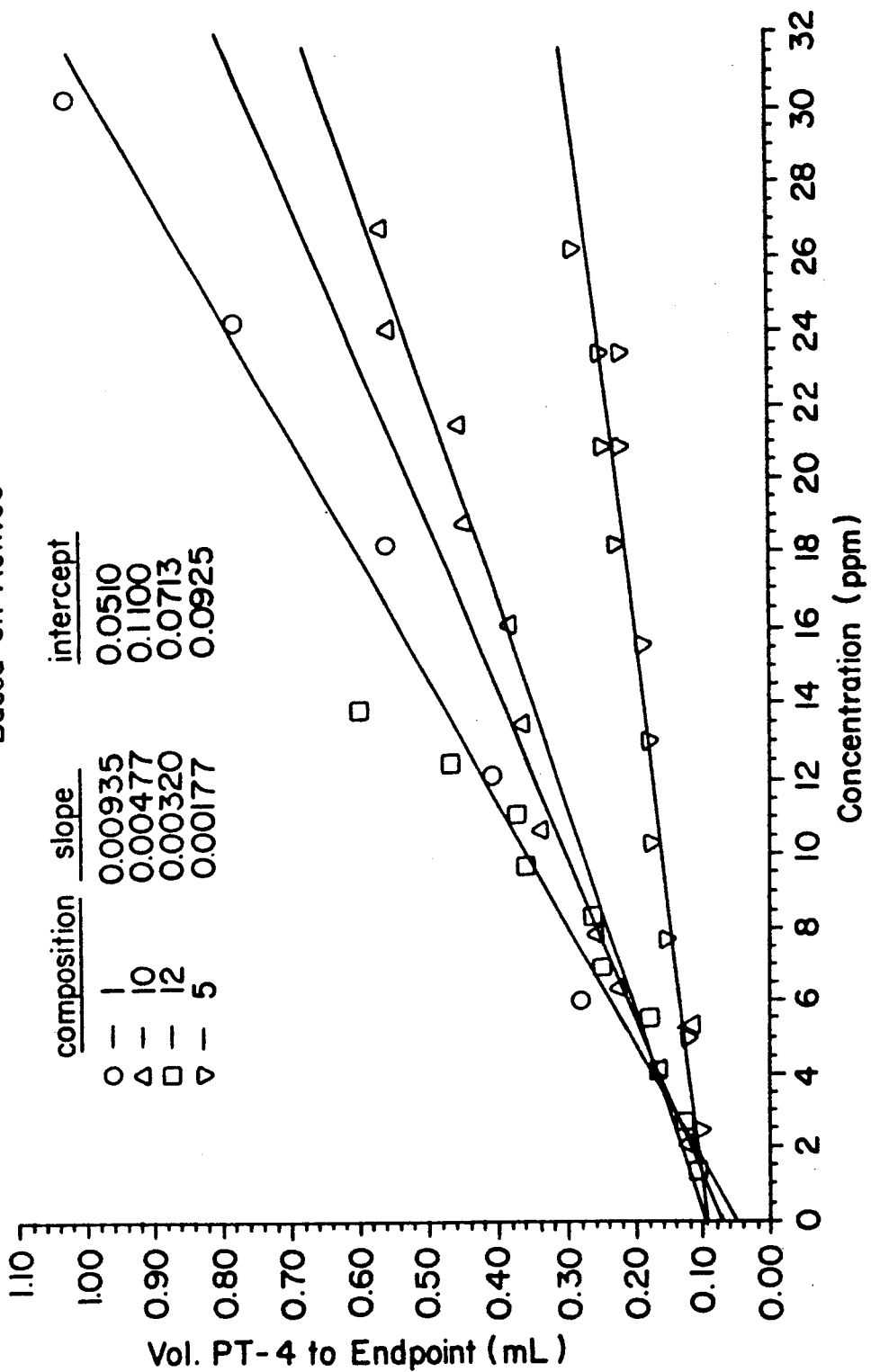

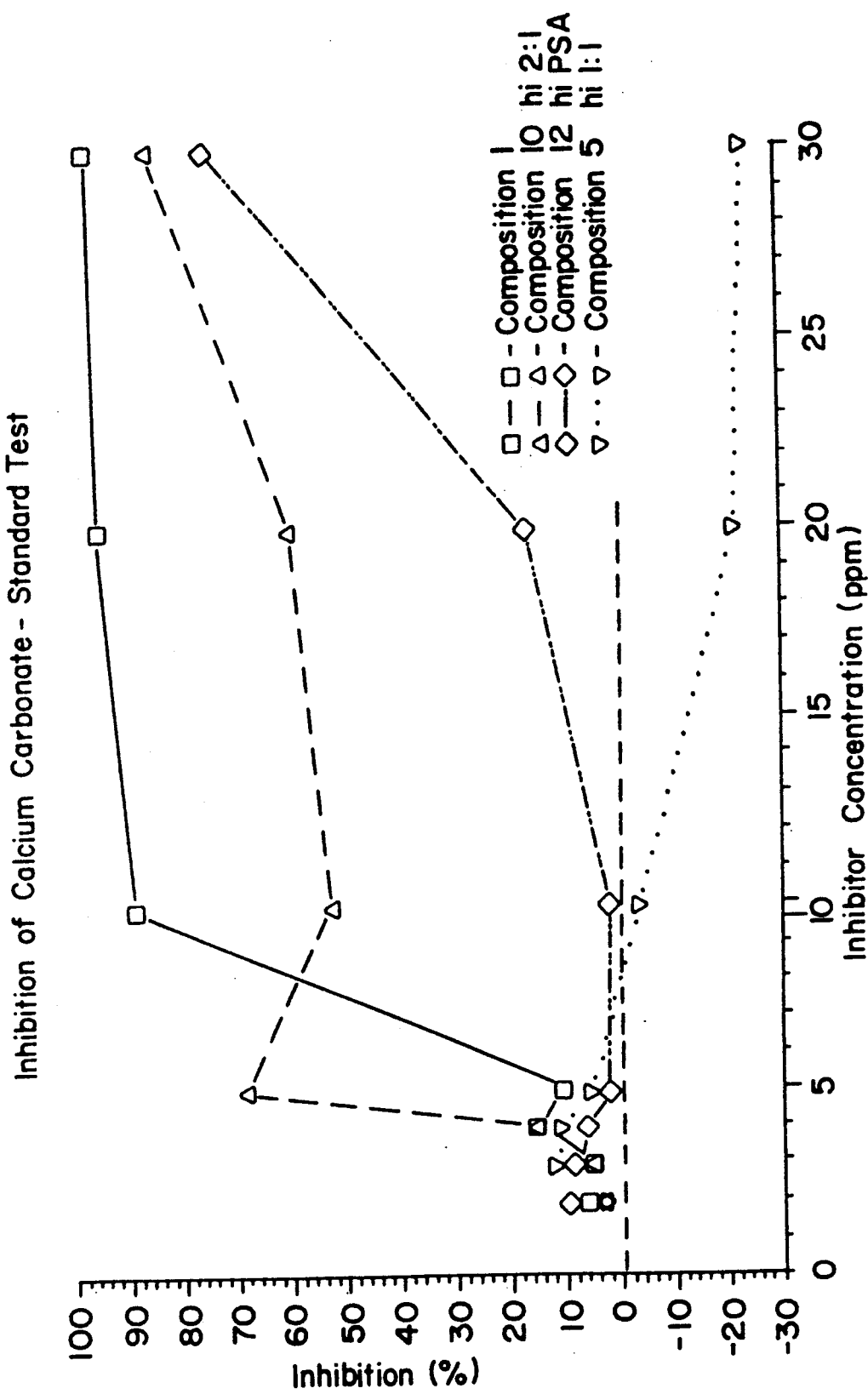

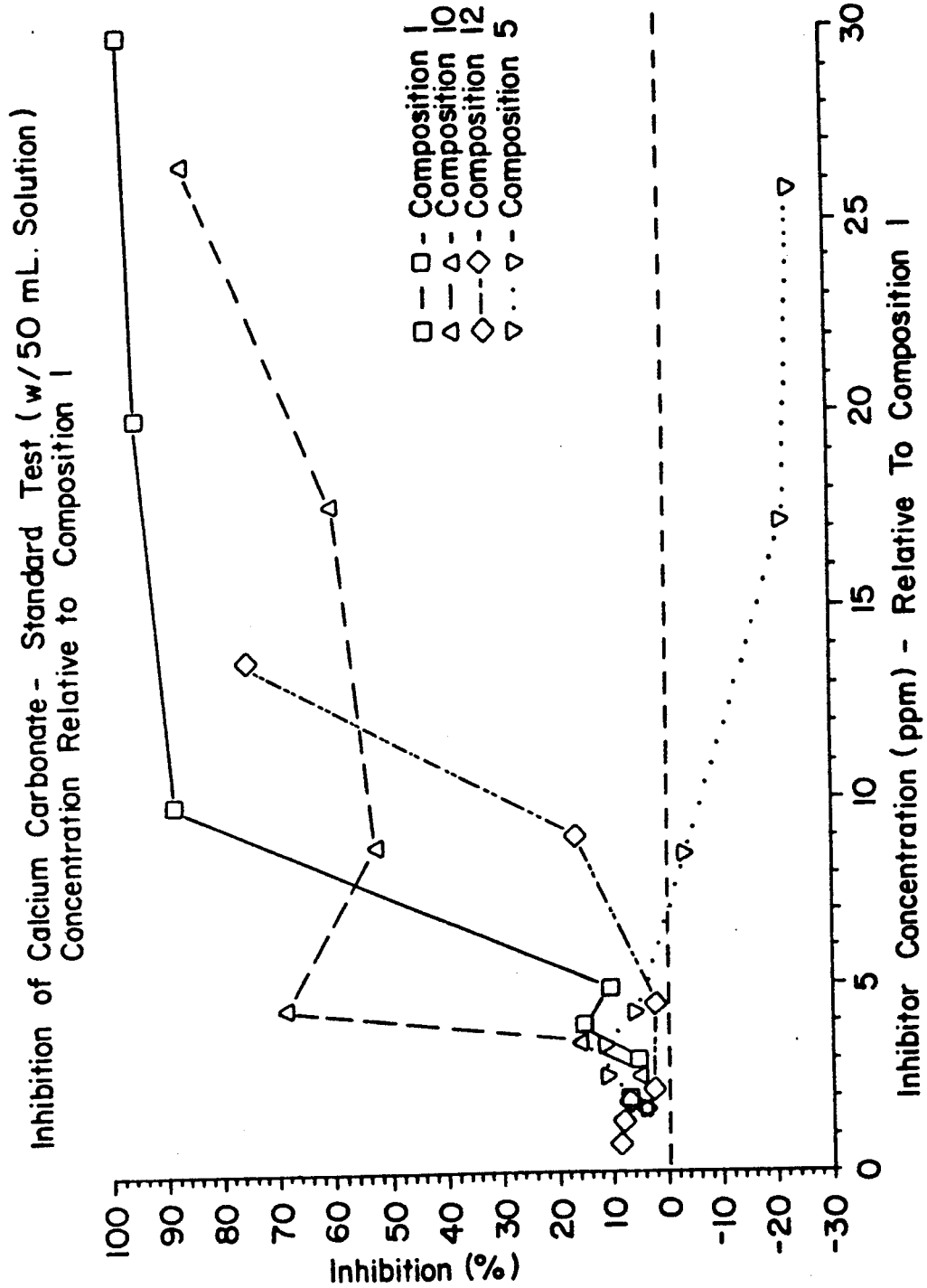

PHOSPHINATE INHIBITOR FOR SCALE SQUEEZE APPLICATIONS

BACKGROUND OF THE INVENTION

Chemical scales that result from the deposition of solid salts from supersaturated solutions frequently lead to lost production or abandonment of production wells. Deposits can plug the wellbore, tubing string, downhole safety valves and other valves, and casing perforations. Subsurface pumps can stick and the operation of surface lines and equipment can be restricted.

Deposition can be initiated by a variety of factors, including pressure, pH, and temperature changes, turbulence, surface characteristics, or mixing of incompatible fluids. Incompatible fluids are frequently encountered during waterflooding operations. A common factor that causes scale is pressure reduction encountered by fluids as they enter the wellbore during production. The partial pressure of $CO_2$ in a $CO_2$ saturated brine decreases. Precipitation of $CaCO_3$ results.

A variety of scales, both organic and inorganic, cause production problems. Common inorganic scales are calcium and magnesium carbonate, calcium, magnesium, barium, and strontium sulfate, and iron sulfides. The calcium salts are the most common. Barium scales ar especially difficult to prevent and remove.

Scales can either be removed or inhibited. Walls can also be re-perforated in order to circumvent the plugged area. Most plugging is at the perforation, where pressure changes are first seen. The well can also be fractured in order to bypass previously scaled areas. Both re-perforation and fracturing are expensive and only temporary remedies since scale will rapidly re-form.

Well clean-out can be mechanical or chemical, both of which are expensive. They both involved well shut-in during the cleaning operation. Scales are dissolved by acid treatments, base treatments, two stage treatments (bases followed by acids), and chelants such as EDTA (ethylendiaminetetraacetic acid). Chemicals can be converters or dissolvers. Converters, both inorganic and organic, form solid reaction products. Inorganic converters are usually preceded by an acidizing stage. Organic converters usually form dispersions or pumpable sludges, formed when the scales slough off from the surfaces. Better scale penetration is generally seen due to this sloughing. An acidizing stage generally follows the organic converter treatment. "Solvents," such as chelants, are more expensive but generally more effective.

Scales can be kept from forming by dilution. Fresh brine or a solubility-increasing brine can be injected into the formation to dilute the connate fluid past the solubility limit of the scalant. This procedure is also expensive.

The most efficient way of dealing with scale is to inhibit its formation. Chemicals can be sequestrants or work as threshold inhibitors. Sequestrants form combination pairs with a species normally involved in precipitation, such as calcium ions. The interaction with the sequestrant is on molar basis and therefore requires a large amount of chemical. While effective, this procedure could be cost limiting.

A much more cost effective chemical treatment is to use a threshold chemical, that is, one that inhibits at a concentration well below equimolar amounts. Threshold chemicals can be effective at concentrations as low as 1/1000th the concentration of the scaling mineral.

Precipitation is a complicated process involving supersaturation, nucleation, and crystal growth. An inhibitor can function by one or more mechanisms. It can interfere with the nucleation process or rate. It can interfere with the can be altered. It can also prevent adhesion of crystals to one another or to metal walls. In order to be effective, the scale inhibitor must be present during the nucleation stage of crystal growth.

The most common classes of inhibitor chemicals are inorganic phosphates, organophosphorous compounds and organic polymers. The common phosphates are sodium tripolyphosphate and hexametaphosphate. Organophosphorous compounds are phosphonic acid and phosphate ester salts. The organic polymers used are generally low molecular weight acrylic acid salts or modified polyacrylamides and copolymers thereof. Phosphonates and polymers are more thermally stable than polyphosphates or phosphate esters. Phosphates hydrolyze at high temperatures forming orthophosphates, the metal salts of which may be more insoluble than the scales that they are intended to inhibit.

The phosphates have low brine solubilities and are therefore frequently injected as solids. They can be injected into the wellbore by bypass feeders, baskets, filter packs and bottom-hole well packs. They can also be placed into the formation through fractures along with the fracturing fluids. The chemical then dissolves slowly, resulting in a steady, low concentration of inhibitor.

The phosphonates and polymers are more water soluble and are therefore used as solutions. Either the wellbore or the formation can be treated. Both batch and continuous methods are used for treating the wellbore. It can also be added as a component of a fracturing fluid. These treatments are not optimum since chemical does not contact the point of initial scale formation—for formation face or casing perforations. However, the tubing string and surface equipment will be treated.

A more efficient and less costly procedure is a "squeeze" treatment, in which the chemical is injected into the formation. Production is halted while chemical is injected at a pressure below frac pressure. The chemical optically penetrates the formation to a distance 1–6 feet radially from the wellbore. Inhibitor will then be released into the wellbore as production is resumed. Ideally, the concentration of inhibitor is constant and low (at a concentration slightly above that required for total inhibition—generally 2–4 ppm). The lifetime of a squeeze depends on the flow rate, oil/water ratio and many other factors but can last for 6 months and even up to 2 years.

Squeeze treatments are generally used for production wells. The chemicals could also be used at injection wells to prevent scaling of the injection brines with reservoir brines (if the brines are incompatible). Plugging can occur at the injection well or can occur as the injection fluids contact the formation brines in the reservoir. The injection well would generally not be squeezed then brine withdrawn from the well. The chemical would travel with the injection brine to the producer, also resulting in inhibition of possible scale there. Injection brines themselves have generally reached maximum precipitation, since they have been at equilibrium for some time. Precipitation occurs when injection brine contacts formation brine in these cases. Frequently, the wells are still only treated at the producer, even when injection brines are being used. However, the chemical should be useful for injection wells also.

The chemical can be physically adsorbed or precipitated. Scale inhibitors are ionic (anionic) in nature. Therefore, the adsorption/desorption is believed to be controlled by electrostatic interactions between the inhibitor and formation minerals. Physically adsorbed chemical is generally retained for a shorter time than a precipitated inhibitor. Another possible mechanism of inhibitor retention is phase trapping. Inhibitor will be present in the brine in unswept areas. This inhibitor will then generally be produced back erratically within a few pore volumes of resumption of flow.

A proppant containing a physically adsorbed inhibitor can be injected into a fracture. The chemical will be released from the proppant as production returns. A similar method involves injection of microparticles of an ion exchange resin into the formation followed by inhibitor injection. The resin holds, then slowly releases, the chemical.

Inhibitors precipitated in the formation by multivalent ions have shown the longest squeeze lives. The concentration of inhibitor produced is controlled by the solubility of the inhibitor salt at a particular flow-rate. The chemical is precipitated with multivalent ions, generally calcium. Precipitation with other ions, such as iron or chromium, has been proposed.

The inhibitor can become exposed to the ions in several ways: First, multivalent ions that naturally occur in the reservoir brine can contact inhibitor solution during injection. Upon setting in the reservoir before production is resumed, multivalents can be ion-exchanged from the reservoir minerals. Secondly, an acidic inhibitor solution can be injected. As the acidic solution contacts calcium carbonate and reacts, calcium will be released and the pH will rise. Precipitation will result. Many sandstone reservoirs contain some carbonate. Also multivalent ions can also be injected with the inhibitor if pH of the injection solution is low. As pH rises due to dilution or neutralization, precipitation will result.

A combination chelation/precipitation method has been proposed. The inhibitor remains soluble during injection due to chelation of added multivalent ions by an added chelant. Upon setting in the reservoir, the equilibrium shifts toward the calcium/inhibitor pair, resulting in precipitation.

One method has been proposed that does not require added ions. A low solubility inhibitor is made soluble by raising the pH of the injecting solution. On dilution and neutralizing, the chemical will fall out of solution.

Other methods of inhibitor placement have been mentioned. One involves a water-dispersible inhibitor injected in a water-in-oil emulsion, which reverts on water contact. It is proposed that organophosphonates can be retained more readily when injected with an adsorption agent (an amine or amine quaternary amxonium salt). Others have proposed that phosphonates adsorption last longer when used in various combinations with polymers. The polymer can be injected with the phosphonate or in alternate slugs.

The residual concentrations of phosphonates and phosphate esters can be easily and accurately determined in oil field brines by a titration method. However, no accurate method exists for field testing of polymer residuals.

Since precipitation squeezes are usually superior to adsorption squeezes, a superior squeeze chemical should be one whose calcium salt has a very low solubility. However, the solubility should not be so low that the concentration or produced inhibitor is below that required for effective scale inhibition.

Also, a inhibitor is needed that will inhibit barium sulfate scale as well as the more common scales. Barium sulfate scale is almost impossible to remove once formed and is becoming a more frequent problem, especially in Alaska and many foreign locations. In locations such as the North Sea, barium and strontium sulfate inhibition is becoming a major problem as waterflooding operations involving sea water increase.

Barium scales are a problem in waterflooding operations where sea water is used as an injection fluid. If the reservoir is high in barium, the sea water, being high in sulfate ion, will result in incompatible fluids (barium sulfate formation) in the reservoir. If the formation is high in calcium, calcium sulfate could result. Waterflooding (secondary recovery) or pressure augmentation—in order to increase production pressure—with other brines (not necessarily sea water) can result in incompatible fluids.

Scale inhibition studies have been carried out with calcium carbonate, calcium sulfate and barium sulfate. The precipitation of the inhibitor with calcium is unrelated to its intended inhibition. The inhibitor should also be capable of being precipitated with other metal ions such as magnesium, iron, chromium, etc.

SUMMARY OF THE INVENTION

An improved squeeze treatment for preventing scale formation from production wells and the formations adjacent to the casing of these wells, said squeeze treatment being of the type wherein production is stopped, a solution containing scale inhibitor is introduced under increased pressure into the wellbore, penetrating the formation adjacent to the wellbore, the improvement which comprises using as the scale inhibitor a predominantly phosphinate containing composition comprising:

| Ingredients | Mole Percent - Less Than |
|---|---|
| A. Monosodium phosphinicobis - (succinic acid) | 22 |
| B. Monosodium phosphinico-succinic acid | 26 |
| C. Sodium phosphonosuccinic acid | 12 |
| D. Sodium phosphate | 5 |
| E. Sodium phosphite | 6 |
| F. Sodium hypophosphite, and | 6 |
| G. A phosphinicosuccinic acid oligomer having the probable structural formula: | |

$$\underset{\underset{COOM}{|}}{+CH}\underset{\underset{COOM}{|}}{-CH)_{m}}\underset{\underset{OM}{|}}{\overset{\overset{O}{\|}}{P}}\underset{\underset{COOM}{|}}{+CH}\underset{\underset{COOM}{|}}{-CH)_{n}}$$

wherein G exceeds 25 mole percent, M is H, Na, K, NH$_4$, amine salts and mixtures thereof and m and n are either 0 or a small whole number with the proviso that either m or n is a small whole number and the sum of m plus n is greater than 2.

THE DRAWINGS

FIG. 1 shows Components of Maleic Acid - Hypophosphite Reaction.

FIG. 2 shows Standardization Curve for Titration of Composition 1 by Titration.

FIG. 3 illustrates Production of Composition 1 from Berea Sandstone Cores.

FIG. 4 shows Production of Composition 1 from Berea Sandstone Cores.

FIG. 5 shows Production of Composition 1 from Berea Sandstone Cores.

FIG. 6 illustrates Production of Composition 1 from Berea Sandstone Cores.

FIG. 7 signifies Cumulative Production of Composition 1 from Berea Sandstone Cores.

FIG. 8 shows Production of Scale Inhibitor from Berea Sandstone Cores.

FIG. 9 shows Production of Scale Inhibitor from Berea Sandstone Cores.

FIG. 10 shows Production of Scale Inhibitor from Berea Sandstone Cores.

FIG. 11 illustrates Production of Scale Inhibitor from Berea Sandstone Cores.

FIG. 12 demonstrates Cumulative Production of Inhibitor from Berea Sandstone Cores.

FIG. 13 illustrates Production of Inhibitor from Berea Sandstone Cores.

FIG. 14 shows Production of Inhibitor from Berea Sandstone Cores.

FIG. 15 shows Production of Inhibitor from Berea Sandstone Cores.

FIG. 16 illustrates Production of Inhibitor from Berea Sandstone Cores.

FIG. 17 shows Precipitation of Composition 1 by Field Brine.

FIG. 18 shows Precipitation of Composition 1 by Field Brine.

FIG. 19 demonstrates Precipitation of Composition 1 by Field Brine.

FIG. 20 illustrates Precipitation of Composition 1 by Field Brine.

FIG. 21 illustrates Precipitation of Composition 1 by Field Brine.

FIG. 22 Standardization Plot of Composition 1 Components.

FIG. 23 shows Standardization Plot of Composition Components - Based on Actives.

FIG. 24 Inhibition of Calcium Carbonate - Standard Test.

FIG. 25 Inhibition of Calcium Carbonate - Standard Test (w/ 50 mL. Solution) Concentrations Relative to Composition 1.

PREFERRED EMBODIMENTS OF THE INVENTION

In a preferred embodiment of the invention, a low or a high calcium brine flush follows the introduction of the predominantly phosphinate inhibitor into the formation. The high calcium brine flush is preferred. Alternatively, as a less preferred mode, is the utilization of a high or low calcium brine flush which precedes the introduction of the predominately phosphinate composition into the formation. High and low calcium brine flushes may precede and follow the treatment with the less inhibitor. The term "high calcium brine" flush means the use of an aqueous solution which contains more than about 1,000 ppm of calcium as calcium plus 2 ion. Typical of high calcium brine flushes would be brine solutions which contain several thousand, up to as much as 6,000 ppm of calcium. Conversely the term "low calcium brine" flush solution means brine solutions which contain about 1,000 ppm or less of calcium plus 2. These solutions may have a calcium content as low as 500 ppm, although typically they are at about 1,000 ppm.

In many instances it may be beneficial to follow the calcium preflush or precede the calcium postflush with a so-called pad. The pad is a low hardness brine that isolates the inhibitor slug from the calcium containing pad, preventing possible inhibitor precipitation too close to the wellbore. This process may allow mixing of the inhibitor and calcium slugs further out in the formation. This pad treatment is extremely beneficial when it precedes the high calcium brine postflush.

One of the major advantages of the invention is that it is especially effective at preventing barium scales.

The Oligomer Containing Phosphinate Compositions

Relatively inexpensive organophosphorous scale inhibiting compositions are those disclosed in U.S. Pat. No. 4,088,678. This patent purports to disclose a method for the preparation of monosodium phosphinicobis(succinic acid). It also purports to show this compound as possessing activity as a scale inhibitor. The same concepts are shown in more detail in its British counterpart, GB 1,512,440. The disclosures of these patents are incorporated herein by reference.

Both patents teach preparing its phosphinicobis(succinate) composition by reacting maleic acid with sodium hypophosphite in the presence of a water soluble initiator. The patents demonstrate that the optimum molar ratio of maleic acid to the hypophosphite is 2.2. They clearly indicate that further excesses of the maleic acid do not result in an improved product.

In duplicating the experimental work described in the U.S. and British patents, it first was ascertained the products formed using a molar ratio of maleic acid to hypophosphite of 2.0 were in fact mixtures of products. Secondly, the active component that prevents scale formation is an oligomeric species. Finally, if the oligomeric species are not present in the compositions, there is poor scale inhibition or chelation. The structure of the products produced by reacting maleic acid and hypophosphite are shown in FIG. 1.

Ingredient G in the predominately phosphinate containing composition in the practice of the invention, should exceed 25 mole percent. It may be, and preferably is, between 35–40 mole percent. In most instances M will be Na but may also be H, K, $NH_4$ or amine salts and mixtures thereof.

The structure previously described is considered to be Probable, since due to the nature of the reactants, there is a possibility that a small amount of oligomer would contain random phosphorus atoms in the chain. Also it is known that the compounds related to the above oligomer tend to decarboxylate in the presence of strong oxidizing agents such as peroxides. Neutralization of the phosphinate product at the time of production or formulation into a water treatment composition has been demonstrated to minimize such decarboxylation.

The oligomer containing compositions of the invention may be prepared using the preparative technique set forth in U.S. Pat. No. 4,088,678 and the disclosure of which is incorporated herein by reference. Also incorporated by reference is the disclosure of GB 1,512,440. In using the preparative techniques of these patents it is necessary to react at greater than 2.2 but less than 3 moles of maleic acid or its equivalent salts, anhydride or esters with one mole of sodium or other water soluble hypophosphite in order to produce the high oligomer containing compositions. A preferred ratio of maleic acid to water soluble hypophosphite is between 2.3–2.5.

The high oligomer containing products are only capable of being produced when the maleic acid is in excess to the hypophosphite during the course of the reaction. When the maleic acid is added to the hypophosphite incrementally, or continuously over a period of time, poor yields of the oligomer are obtained. As stated, the preparative technique set forth in U.S. Pat. No. 4,088,678 may be used. The compositions as produced by the process of the patents are aqueous solutions containing between about 35–40% solids. A preferred composition of the invention, hereafter referred to as Composition 1, may be prepared in accordance with the following method.

Preparation of Composition 1

Maleic anhydride (1407.4 g, 14.36 moles) (crushed briquettes) was dissolved in water (2279.1 g) at room temperature or slightly above. The exothermic hydrolysis of maleic anhydride brought the temperature up to 30° C. To this solution was added sodium hypophosphite monohydrate (691.89 g, 6.53 moles) which dissolved with a mild exotherm raising the temperature of the reaction to 38° C. Nitrogen purging was begun and the reaction mixture was then heated to 60° C. to complete the dissolution of hypophosphite. (Solids remained undissolved below 60° C.). The freshly prepared amxonium persulfate solution (176.82 g dissolved in 412.58 g of water) was added continuously into the maleic acid-hypophosphite solution over a six (6) hour period while maintaining the reaction temperature at 60° C. There was a mild exotherm which was controlled with cooling as needed to prevent too rapid consumption of initiator. After initiator addition was completed, the reaction was stirred and held at 60° C. for 2.5 hours. At the end of this time (8.5 hours), the reaction mixture was checked for the presence of residual peroxides using a starch-iodide test. If the test was positive, heating of the reaction was continued raising the temperature to 70° C. and holding for one hour more. The reaction mixture was tested for peroxides at half-hour intervals during the one hour holding time. After this heating period, if the peroxide test was still positive, temperature was increased to 80° C. and held until a negative peroxide test was obtained. The reaction mixture was then cooled to 25° C. Concentration of the product was calculated as 45.4% on the basis that all maleic acid and sodium hypophosphite (non-hydrated) had reacted.

The cooled reaction mixture (4934.3 g) was neutralized to pH7 with 50% sodium hydroxide (2220.1 g) while maintaining the temperature at or below 60° C. The neutralized product was then cooled to 25° C. and was filtered to remove undissolved material. Concentration of the neutralized product (expressed as the acid form) was 31.31%.

The reaction mixture was examined using $^{13}$C NMR and $^{31}$P NMR. Carbon - 13 NMR spectra of this Composition 1 sample showed that all maleic acid had reacted including the ten mole percent excess over the sodium hypophosphite that was used. Compositions of Composition 1 samples were determined using $^{31}$P NMR. Examples of typical compositions useful in the practice of the invention are shown below in Table 1 which lists Compositions 1–15. Also listed are Compositions 16–26. Several of the Compositions in Table 1 and Compositions 16–26 are not the phosphinates of the invention but are compared against them in the examples hereafter presented.

TABLE 1

COMPOSITION OF MALEIC ACID/HYPOPHOSPHITE SAMPLES DETERMINED BY $^{31}$P NMR

| COMPO-SITION # | RATIO (MALEIC/NaH$_2$PO$_2$) | ACTIVES (%) | OLIGO-MER | MOLE % 2:1 | MOLE % 1:1 | PSA | H$_2$PO$_2^{-1}$ | HPO$_3^{-2}$ | PO$_4^{-2}$ | UN-KNOWN | COMMENTS |
|---|---|---|---|---|---|---|---|---|---|---|---|
| 1 | 2.2/1 | 30.40 | 35.5 | 23.3 | 23.7 | 8.7 | 4.2 | 2.2 | | 2.4 | |
| 2 | 2.5/1 | 30.8 | 40.5 | 17.6 | 22.0 | 9.0 | 3.2 | 2.8 | 0 | 4.9 | pH 7 |
| 3 | 2.2/1 | 31.6 | 32.9 | 21.9 | 25.9 | 8.9 | 4.2 | 2.6 | 0 | 3.6 | pH 7 |
| 4 | 2.2/1 | 31.6 | 24.6 | 55.7 | 14.2 | 2.7 | 0 | 2.8 | 0 | 0 | pH 7; Semi-batch |
| 5 | 1.0/1 | 22.93$^f$ | 0 | 12.8 | 67.0 | 0 | 15 | 5.1 | 0 | 0 | $^a$ $^g$; pH 7 |
| 6 | 2.2/1 | 45.8 | 31.7 | 19.0 | 25.6 | 9.7 | 5.8 | 4.2 | 0 | 4.0 | Unneutralized Composition 15 |
| 7 | 2.5/1 | 44.8 | 40.5 | 17.6 | 22.0 | 9.0 | 3.2 | 2.8 | 0 | 4.9 | Unneutralized Composition 2 |
| 8 | 2.1/1 | | 37.4 | 18.6 | 26.2 | 6.2 | 6.1 | 3.5 | 0 | 2.0 | |
| 9 | 2.1/1 | | 27.6 | 19.0 | 23.2 | 13.4 | 4.0 | 6.9 | 0 | 5.3 | |
| 10 | 2.0/1 | 6.91 | 15.1 | 49.6 | 31.0 | 1.5 | 1.0 | 1.8 | 0 | 0 | $^a$; Semi-batch |
| 11 | 1.0/1 | 15.27$^b$ | 0 | 12.8 | 67.1 | 0 | 15.0 | 5.1 | 0 | 0 | pH 7 |
| 12$^e$ | | 11.54$^c$ | 0 | 14.3 | 1.9 | 59.3 | 0 | 3.8 | 20.6 | 0 | pH 7 |
| 13$^e$ | | 20.37$^d$ | 0 | 14.1 | 7.7 | 55.7 | — | 7.4 | 15.1 | | pH 7 |
| 14 | 3.0/1.0 | | 40.6 | 15.4 | 20.2 | 10.8 | 4.6 | 3.0 | 0 | 5.4 | |
| 15 | 2.2/1 | 31.5 | 31.7 | 19.0 | 25.5 | 10 | 6 | 4 | 0 | 4 | pH 7 |

$^a$Maleic + persulfate added to NaH$_2$PO$_2$
$^b$Concentration as 1:1 adduct only
$^c$Concentration of PSA only
$^d$Concentration as if all P is in PSA
$^e$Oxidized Composition 5
$^f$Concentration of all P compounds as actives
$^g$Concentration of all P compounds as actives; in acid form is 28.2%

Composition 16: phosphate ester of diethanol/triethanol amine, sodium salt, 34% active as acid Composition 17: phosphate ester of triethanol amine Composition 18: copolymer of acrylic acid and methacrylic acid, sodium salt, 18% active as acid, M.W.=46,000

Composition 19: phosphonomethylated hexamethylenediamine residue, partial sodium salt, 46.1% active Composition 20: acrylic acid/methyl acrylate/thioglycolic acid copolymer, 25.3% active, M.W.=2,000–2,500

Composition 21: phosphonomethylated diethylenetriamine, partial sodium salt, 22.3% active Composition 22: sodium polyacrylate 17.6%

Composition 23: phosphonomethlyated monoamine, 19.9 or 21.0%

Composition 24: phosphonomethylated ethylenediamine, partial NH₄ salt, 26.6%

Composition 25: phosphonomethylated diethylenetriamine, acid=17.0%, partial sodium salt=18.6%

Composition 26: sodium vinyl sulfonate, 24.64% polymer

| COMP. 1 SAMPLE NUMBER | 2:1 | OLIG | 1:1 | PSA | UNK | H₂PO₂⁻ | H₃PH₃ |
|---|---|---|---|---|---|---|---|
| A | 19.0 | 27.6 | 23.2 | 13.4 | 5.3 | 4.6 | 6.9 |
| B | 18.6 | 37.4 | 26.2 | 6.2 | 2.0 | 6.1 | 3.5 |
| C | 17.4 | 26.7 | 31.8 | 8.8 | 3.7 | 7.0 | 4.6 |
| D | 21.9 | 32.9 | 25.9 | 8.9 | 3.6 | 4.2 | 2.6 |
| E | 23.3 | 35.5 | 23.7 | 8.7 | 2.4 | 4.2 | 2.2 |

2:1 - monosodium phosphinicobis (succinic acid)
OLIG - oligomeric maleic-phosphinic compounds
1:1 - monosodiumphosphinicosuccinic acid
PSA - monosodium phosphonosuccinic acid
UNK - unidentified phosphonic compound
H₂PO₂⁻ - unreacted sodium hypophosphite
H₃PH₃ - phosphorous acid Another method to produce the compositions containing higher oligomer content materials is set forth below.

Preparation

High Oligomer Content Products

Maleic anhydride (306.25 g, 3.125 moles) briquettes were crushed and added to a 1.5-liter reaction flask along with about 516.9 g of water. The suspension was stirred for about 15 minutes as the maleic anhydride dissolved and hydrolyzed, raising the temperature of the solution from 21° C. to 32° C. After stirring for 45 minutes longer, the mild exotherm began to subside and sodium hypophosphite monohydrate (132.5 g, 1.25 moles) was added. A second mild exotherm occurred as sodium hypophosphite dissolved. Nitrogen purging was begun and the reaction mixture was heated to 60° C. over 30 minutes. Ammonium persulfate solution was added (99.75 g of a 37.22% aqueous solution) over about four hours. Temperature was controlled at 60-61° C. using heating or cooling as needed. When addition of the catalyst was complete, heating at 60° C. was continued for 2.5 hours longer. Heating was continued and incrementally increased to 80° C. until oxidant was consumed or destroyed, as indicated by a negative starch-iodide test. The clear, yellow solution was highly acidic (pH 1). The concentration of the final product before neutralization was 44.77% (assuming complete incorporation of maleic acid and sodium hypophosphite). Analysis of the reaction mixture was done using −P and $^{13}$C NMR, showing the absence of maleic acid in the final product mixture. Composition of this reaction mixture is shown in Table 1 as Composition 2.

A sample (100.0 g of the 44.77% solution described above) was neutralized to pH 7.0 by dropwise addition of the 50% sodium hydroxide. Temperature of the solution was observed and maintained at 60° C. or less with ice-water bath cooling. The concentration of the resultant solution was 30.79% (calculated based on dilution).

Using the above preparative technique as well as what may be referred to as a semi-batch procedure, in which the maleic acid was added simultaneously with the initiator, a variety of product compositions were prepared. The results of these preparations are shown in Table 1. This Table also shows poor oligomer yields when the preferred preparative method is not followed.

The compositions used in the practice of the invention are in the form of aqueous solutions which have been neutralized with a water soluble base such as sodium hydroxide to prevent decarboxylation from occurring. These neutralized compositions usually will be neutralized to a pH of around 7-7.5.

Application of the Compositions in Well Squeeze Treatments

As indicated, the oligomer containing compositions used in the practice of the invention are aqueous solutions. Under conditions of field use they are usually utilized in the form of solutions ranging in strength from about 5-20 % by weight. A typical solution used to squeeze treat injection wells would be about 10% by weight.

The amount of the inhibitor placed into the wellbore to treat the well equipment, as well as the formation itself adjacent to the well casing, would be that axount sufficient to penetrate between 5-7 feet into the formation. This particular dosage can be readily calculated using known techniques. Similarly, the pressure used to inject the chemical is such that fracturing pressure is not exceeded. After injection, the reservoir should be set-in for 12 hours or overnight. Production is then resumed. To demonstrate the efficiency and efficacy of the invention, the following are presented by way of example.

Examples

The analyses for the concentrations of Composition 1 could be determined by a complexometric titration method for determining the amount of organophosphorus compounds. The standardization plot for Composition 1 is shown in FIG. 2.

Calcium carbonate and calcium and barium sulfate deposition tests were done according to the standard procedures set forth below:

TEST METHOD 1

Calcium Carbonate Deposition Test

Apparatus

1. Constant temperature bath (100° to 200° F.)
2. Glass test cells (4 oz. bottles with screw lid)
3. Synthetic brines
   A. 12.16 gms/L CaCl₂.2H₂O 3.68 gm/L MgCl₂.6H₂O 33 gm/L NaCl
   B. 7.36 gms/L NaHCO₃ 29.4 mg/L Na₂SO₄ 33 gm/L NaCl
4. Graduated cylinders 2-50 ml
5. Appropriate solutions of inhibitors to be tested
6. Pipettes: 1-0.1 ml, 1-1.0 ml and 1-10 ml
7. 125 ml Erlenmeyer flasks for each inhibitor to be tested
8. Standard EDTA solution (1 ml=1 mg of CaCO₃)
9. 6 Normal sodium hydroxide
10. Ammonium purpurate indicator
11. 10 ml micro buret Procedure 1. Using the appropriate solutions of inhibitors, pipette the desired amount of inhibitor into each test cell.
2. Two controls (blanks) are set up with each test. Control contains no inhibitor.

3. Brines A and B should be saturated with $CO_2$ for thirty minutes before using.
4. Add 50 ml of Brine A and B to each test cell.
5. Cap test cells and agitate to thoroughly mix brines and chemicals.
6. Put test cell in water bath at 160° F. for 24 hours.
7. After exposure at the 160° temperature for 24 hours, the test cells are removed and allowed to cool to room temperature.
8. pipette 1 ml of the brine from each test cell and transfer to the Erlenmeyer flask.
9. Add 50 ml of distilled water to the Erlenmeyer.
10. Add 1 ml of 6N sodium hydroxide.
11. Add a small amount of ammonium purpurate indicator and titrate with the EDTA solution. The color changes from pink to violet.
12. The amount of $CaCO_3$ retained in solution is computed by multiplying the ml of standard EDTA solution used by 1000. The results are expressed as calcium carbonate.
13. A typical scale evaluation is found below:

| Chemical | Calcium Carbonate Retained in Solution (mg/L) | | | | |
| --- | --- | --- | --- | --- | --- |
| | 1 ppm | 3 ppm | 5 ppm | 10 ppm | 20 ppm |
| A | 3,000 | 3,400 | 3,800 | 4,000 | 4,300 |
| B | 3,500 | 4,000 | 4,100 | 4,100 | 4,100 |
| C | 3,600 | 4,300 | 4,300 | 4,300 | 4,300 |
| Blank (after precipitation) | 2,600 mg/l as $CaCO_3$ | | | | |
| Blank (before precipitation) | 4,300 mg/l as $CaCO_3$ | | | | |

14. Test results may also be recorded in percent inhibition as illustrated below.

| Chemical | Test Results in Percent Inhibition | | | | |
| --- | --- | --- | --- | --- | --- |
| | 1 ppm | 3 ppm | 5 ppm | 10 ppm | 20 ppm |
| A | 24 | 46 | 71 | 82 | 100 |
| B | 53 | 82 | 88 | 88 | 88 |
| C | 69 | 100 | 100 | 100 | 100 |
| Blank (after precipitation) | 2,600 mg/l as $CaCO_3$ | | | | |
| Blank (before precipitation) | 4,300 mg/l as $CaCO_3$ | | | | |

TEST METHOD 2

Calcium Sulfate Deposition Test

Apparatus

1. Constant temperature water bath (100° to 200° F.)
2. Glass test cells (4 oz. bottles with screw lids)
3. Synthetic brines
   A. Calcium brine; 7.5 gms/L USP NaCl 11.1 gms/L $CaCl_2.2H_2O$
   B. Sulfate brine; 7.5 gms/L UPS NaCl 10.66 gms/L $Na_2SO_4$
4. Graduated cylinders 2-50 ml
5. Appropriate solutions of inhibitors to be tested
6. Pipettes: 1-0.1 ml, 1-1.0 ml and 1-10 ml
7. 125 ml Erlenmeyer flasks for each inhibitor to be tested
8. Standard EDTA solution (1 ml = 1 mg of $CaCO_3$)
9. 6 Normal Sodium Hydroxide
10. Ammonium purpurate indicator
11. 10 ml micro buret Procedure 1. Using the appropriate solutions of inhibitors, pipette the desired amount of inhibitor into each test cell.
2. Two controls (blanks) are set up with each test. Controls contain no inhibitor.
3. Add 50 ml of calcium chloride brine to each cell.
4. Add 50 ml of sodium sulfate brine to each cell.
5. Cap test cells and agitate to thoroughly mix brines and chemicals.
6. Put test cell in water bath at 160° F. for 24 hours.
7. After exposure at the 160° temperature for 24 hours, the test cells are removed and allowed to cool to room temperature.
8. Pipette 1 ml of the brine (pipette off the top so any calcium sulfate crystals will not be included) and transfer to the Erlenmeyer flask.
9. Add 50 ml of distilled water to the Erlenmeyer flask.
10. Add 1 ml of 6N Sodium Hydroxide.
11. Add a small amount of ammonium purpurate indicator and titrate with the standard EDTA solution. The color changes are from pink to violet.
12. The axount of calcium sulfate retained in solution is computed by multiplying the ml of standard EDTA solution used by 1000.
13. The standard API test method for calcium may be used as an alternate method.
14. A typical scale evaluation is found below:

| Chemical | CALCIUM SULFATE RETAINED IN SOLUTION AS CALCIUM CARBONATE (mg/L) | | | | |
| --- | --- | --- | --- | --- | --- |
| | 1 ppm | 3 ppm | 5 ppm | 10 ppm | 20 ppm |
| A | 4000 | 4000 | 4000 | 4000 | 4000 |
| B | 3000 | 3200 | 3600 | 3800 | 4000 |
| C | 3600 | 3900 | 4000 | 4000 | 4000 |
| Blank (after precipitation) | 2800 mg/l as $CaCO_3$ | | | | |
| Blank (before precipitation) | 4000 mg/l as $CaCO_3$ | | | | |

15. Test results may also be recorded in percent inhibition as illustrated below:

| Chemical | Test Results in Percent Inhibition | | | | |
| --- | --- | --- | --- | --- | --- |
| | 1 ppm | 3 ppm | 5 ppm | 10 ppm | 20 ppm |
| A | 100 | 100 | 100 | 100 | 100 |
| B | 17 | 33 | 67 | 83 | 100 |
| C | 67 | 92 | 100 | 100 | 100 |
| Blank (after precipitation) | 2800 mg/l as $CaCO_3$ | | | | |
| Blank (before precipitation) | 4000 mg/l as $CaCO_3$ | | | | |

TEST METHOD 3

Standard Barium Sulfate Scale Deposition Test Procedure

Solution 1. 1% or 0.1% distilled water solutions of the chemicals being tested.
2. Brine X
   42 grams of sea salt dissolved in distilled water to make one liter of Brine X
   Sea-Salt (ASTM D-1141-52)
3. Brine Y
   25 grams of analytical grade sodium chloride and 0.0456 grams of analytical grade $BaCl_2.2H_2O$ dissolved in distilled water to make one liter of Brine Y.
4. Brine Z 50 grams of analytical grade NaHCO$_3$ dissolved in distilled water to make one liter of Brine Z.

Scale squeeze simulation studies used Berea sandstone cores. Cores were 1'×3" rods, 300–600 md permeability, 21% porosity and had been cut parallel to the bedding plane. The cores were prepared by oven drying under vacuum for one day and were epoxy encased. They were evacuated, saturated with brine, oil-flooded (with kerosene) until no more water was expelled, then waterflooded to irreducible oil saturation (waterflooded residual oil conditions).

Prepared cores were equilibrated at 100° F., the inhibitor solution (called a slug) was injected into the core, either preceded (preflush) and followed by (postflush) or only followed by a slug containing a brine high in calcium ion. The saturation brine in all of the tests was 8 percent NaCl and 1,000 ppm calcium. The inhibitor slug contained 9% NaCl, but no calcium, except for the acid squeeze procedure. The inhibitor slug contained 10% Composition 1. The brine used to set in the inhibitor contained 5450 ppm calcium (2% CaCl$_2$.H$_2$O). The core was set overnight then flooded with the saturation brine at 2 mL/min. Production flow was in the direction opposite from inhibitor injection at a rate of from 0.7–2 mL/min. The same brine used for saturations was used as drive brine. Effluent samples were collected and analyzed for inhibitor concentration. The pressures at each stage of floods were measured. From pressures and flow rates, permeabilities were calculated. It was important that the precipitation of the inhibitor not cause adverse permeability reductions.

RESULTS AND DISCUSSION

Scale Inhibition

Composition 1 was effective in inhibiting calcium carbonate, calcium sulfate and barium and strontium sulfate as Tables 2–7 show.

TABLE 2

STANDARD CALCIUM CARBONATE SCALE DEPOSITION TESTS
PERCENT INHIBITION

| COMPOSITION # | INHIBITOR CONCENTRATION (ppm) | | | | | | | | | |
|---|---|---|---|---|---|---|---|---|---|---|
| | 1 | 2 | 3 | 4 | 5 | 6 | 8 | 10 | 15 | 50 |
| 16 | 75/20 | 100/87 | 100/100 | | | | | | | |
| 18 | | | | 47 | 66 | 94 | 94 | 100 | | |
| 19 | 66 | 78 | 91 | 94 | 100 | | | | | |
| 21 | | | | | 63 | 81 | 100 | 100 | | |
| 22 | | | | | | | 56 | 88 | 100 | |
| 23 | | | 44 | 69 | 75 | 88 | 94 | 100 | | |
| 24 | | | | 75 | 97 | 97 | 100 | | | |
| 1 | | | 93 | | 100 | | | | | |
| 3 | | | 93 | | 100 | | | | | |
| 2 | | | 93 | | 100 | | | | | |
| 4 | | | 87 | | 93 | | | 100 | | |

TABLE 3

STANDARD CALCIUM SULFATE SCALE DEPOSITION TESTS
PERCENT INHIBITOR

| COMPOSITION # | INHIBITOR CONCENTRATION (ppm) | | | | | | | | | | |
|---|---|---|---|---|---|---|---|---|---|---|---|
| | 0.1 | 0.2 | 0.3 | 0.4 | 0.5 | 0.6 | 0.8 | 1.0 | 1.5 | 2.0 | 3.0 |
| 16 | 8 | 75/67 | 100/100 | | | | | | | | |
| 18 | | | | | | | | 20 | 70 | 100 | |
| 19 | | | 20 | 50 | 85 | 100 | | | | | |
| 21 | | 10 | 35 | 50 | 80 | 95 | 100 | | | | |
| 22 | | | | | | | | | 40 | 55 | 100 |
| 23 | | | | | | | | | 65 | 100 | |
| 24 | | | | 70 | 90 | 100 | | | | | |
| 1 | | | 33 | | 92 | | | 100 | | | |
| 3 | | | 33 | | 92 | | | 100 | | | |
| 2 | | | 42 | | 92 | | | 100 | | | |
| 4 | | | 50 | | 83 | | | 92 | | 100 | |

TABLE 4

STANDARD BARIUM SULFATE SCALE
DEPOSITION TESTS
PERCENT INHIBITION

| COMPOSITION # | INHIBITOR CONCENTRATION (ppm) | | | | | | | | |
|---|---|---|---|---|---|---|---|---|---|
| | 0.8 | 1 | 1.5 | 2 | 3 | 5 | 10 | 20 | 50 | 100 |
| 16 | | 40 | 100 | | | | | | | |
| 16 | 38 | 57 | | 98 | 99 | | | | | |
| 17 | | | 25 | | 35 | | 95 | 100 | | |
| 18 | | | | | 27 | | 22 | | | 55 |
| 18 | | | | | 64 | 96 | 100 | | | |
| 20 | | | | | | | 2 | | 17 | 24 |
| 1 | | | | | | 94 | 99 | 99 | 100 | |
| 3 | | | | | | 84 | 99 | 100 | 100 | |
| 2 | | | | | | 78 | 99 | 100 | 100 | |
| 4 | | | | | | 13 | 81 | 99 | 100 | |

TABLE 5

BARIUM SULFATE SCALE DEPOSITION STUDIES
PERCENT INHIBITION

| COMPOSITION # | TEMPERATURE (°F.) | BRINE RATIO$^a$ | | | INHIBITOR CONCENTRATION ppm | | | | | | | | Ba$^{+2}$ IN BLANK (PPM) | | pH ADJUSTMENT |
|---|---|---|---|---|---|---|---|---|---|---|---|---|---|---|---|
| | | A | B | C | 1 | 2 | 3 | 5 | 10 | 20 | 30 | 50 | 100 | BEFORE PPM | AFTER PPM | |
| 21 | 180 | 90 | | 10 | 55 | 76 | 100 | 100 | | | | | | 195 | 10 | None |

TABLE 5-continued

BARIUM SULFATE SCALE DEPOSITION STUDIES
PERCENT INHIBITION

| | | | | | | | | | | | | | | | | |
|---|---|---|---|---|---|---|---|---|---|---|---|---|---|---|---|---|
| | | 90 | 10 | | | | 85 | 98 | | 100 | 100 | 100 | 195 | 13 | 5.5 |
| | | 50 | 50 | | | | 0 | 0 | | 71 | 96 | 96 | 114 | 0.5 | None |
| 25 | 180 | 90 | 10 | 5 | 13 | 63 | 97 | 100 | | | | | 195 | 10 | None |
| | | 90 | 10 | | | | 47 | 96 | | 98 | 100 | 100 | 195 | 13 | 5.5 |
| | | 50 | 50 | | | | | | | 59 | 95 | 96 | 114 | 0.5 | None |
| 26 | 180 | 90 | 10 | 5 | 11 | 21 | 53 | 94 | | | | | 195 | 10 | |
| | | 90 | 10 | | | | 74 | 93 | | 100 | 98 | 100 | 195 | 13 | 5.5 |
| | | 50 | 50 | | | | | | | | | 22 | 114 | 0.5 | None |
| 1 | 180 | 90 | 10 | 5 | 8 | 47 | 100 | 100 | | | | | 195 | 10 | None |
| | | 90 | 10 | | | | 36 | 98 | | 100 | 100 | 98 | 195 | 13 | 5.5 |
| | | 50 | 50 | | | | | 2 | | 25 | 96 | 98 | 114 | 0.5 | None |
| 1 | 240 | | 90 | 10 | | | 45 | 90 | 95 | | 97 | | 206 | 20 | None |
| | | 50 | 50 | | | | | 3 | 9 | | 15 | 61 | 108 | 1 | None |
| 18 | 240 | | 90 | 10 | | | 5 | 20 | 73 | | 97 | | 206 | 20 | None |
| | | | 50 | 50 | | | | 9 | 13 | | 24 | 43 | 108 | 1 | None |

| REAGENT | $^a$mg/L FOR SYNTHETIC BRINE | |
|---|---|---|
| | BRINE A (FORMATION BRINE) | BRINE C (SEA WATER) |
| NaCl | 84.179 | 25.650 |
| KCl | 1.057 | 0.431 |
| CaCl$_2$.2H$_2$O | 10.143 | 1.852 |
| MgCl$_2$.6H$_2$O | 3.130 | 11.632 |
| BaCl$_2$.2H$_2$O | 0.407 | — |
| SrCl$_2$.2H$_2$O | 1.263 | 0.0274 |
| Na H CO$_3$ | 1.333 | — |
| NaBr | 0.161 | — |
| Na$_2$SO$_4$ | | 4.192 |
| pH | 6.5 | 8.2 |

NOTE:
Brine B is identical to Brine A except that NaHCO$_3$ and NaBr are absent

TABLE 6

BARIUM SULFATE INHIBITION WITH 50/50 FIELD
BRINE/SEA WATER (SYNTHETIC)$^a$ at 65° C.
PERCENT INHIBITION

| COMPOSITION # | INITIAL pH ADJUSTMENT | INHIBITION CONCENTRATION (ppm) | | | | | |
|---|---|---|---|---|---|---|---|
| | | 5 | 10 | W/HCO$_3$ | 20 | W/HCO$_3$ | 30 | 40 |
| 18 | None | | 32.4 | | | 84.5 | 81.5 | 85.4 |
| 21 | None | | 19.1 | | | 47.5 | 48.4 | 50.9 |
| 1 | None | 10.0 | 83.0 | 88.8 | | 94.8 | 89.2 | 96.6 | 96.6 |
| | | | 85.9 | | | | | |
| | 7 | | 93.1 | | | 93.9 | | |
| | | | 80.5 | | | | | |
| | 8 | | 85.1 | | | 95.6 | | |
| | | | 61.8 | | | | | |

| | $^a$g/L IN DEIONIZED WATER | |
|---|---|---|
| | FIELD BRINE | SEA WATER |
| NaCl | 22.388 | 22.388 |
| CaCl$_2$.2H$_2$O | 1.099 | |
| MgCl$_2$.6H$_2$O | 6.016 | |
| BaCl$_2$.2H$_2$O | 0.082 | |
| Na$_2$SO$_4$ | | 20.030 |

Ba$^{+2}$ before precipitation = 24.25 mg/L
Ba$^{+2}$ after precipitation = 0.40 mg/L

TABLE 7

STRONTIUM SULFATE SCALE DEPOSITION STUDIES
180° F.
PERCENT INHIBITION

| COMPOSITION # | BRINE RATIO$^a$ | | INHIBITOR CONCENTRATION (ppm) | | | | | | | | Sr$^2$ IN BLANK (ppm) | | pH ADJUSTMENT |
|---|---|---|---|---|---|---|---|---|---|---|---|---|---|
| | A | C | 1 | 2 | 3 | 5 | 10 | 30 | 50 | 100 | BEFORE ppm | AFTER ppm | |
| 21 | 90 | 10 | | 86 | 86 | 100 | 100 | | | | 355 | 320 | None |
| | 90 | 10 | | | | 84 | 94 | 100 | 100 | 100 | 350 | 318 | 5.5 |
| | 50 | 50 | | | | 36 | 48 | 96 | 100 | 100 | 210 | 85 | None |
| 25 | 90 | 10 | 14 | 14 | 71 | 100 | 100 | | | | 355 | 320 | None |
| | 90 | 10 | | | | 59 | 97 | 94 | 100 | 97 | 350 | 318 | 5.5 |
| | 50 | 50 | | | | | | 92 | 100 | 100 | 210 | 85 | None |
| 26 | 90 | 10 | 0 | 0 | 14 | 57 | 57 | | | | 355 | 320 | None |
| | 90 | 10 | | | | 84 | 97 | 100 | 94 | 100 | 350 | 318 | 5.5 |
| | 50 | 50 | | | | 62 | 71 | 63 | 68 | 88 | 210 | 85 | None |
| 1 | 90 | 10 | 0 | 14 | 57 | 100 | 100 | | | | 355 | 320 | None |
| | 90 | 10 | | | | 41 | 97 | 97 | 100 | 100 | 350 | 318 | 5.5 |

TABLE 7-continued

STRONTIUM SULFATE SCALE DEPOSITION STUDIES
180° F.
PERCENT INHIBITION

| COMPOSITION # | BRINE RATIO[a] | | INHIBITOR CONCENTRATION (ppm) | | | | | | | | $Sr^2$ IN BLANK (ppm) | | pH ADJUSTMENT |
|---|---|---|---|---|---|---|---|---|---|---|---|---|---|
| | A | C | 1 | 2 | 3 | 5 | 10 | 30 | 50 | 100 | BEFORE ppm | AFTER ppm | |
| | 50 | 50 | | | | | 48 | 84 | 100 | 100 | 210 | 85 | None |

[2]SAME BRINES AS USED IN TABLE 5

In fact, this product is superior to most other products tested in treating for all of these scales. The only product tested that is superior to Composition 1 in all of these tests is Composition 16. However, this product is a mixture of phosphate esters which are unstable at higher temperatures. Composition 1 would be expected to be stable at higher temperatures due to the structures of the components.

Core Testing of Composition 1

Tests on Berea sandstone cores have shown a definite advantage of Composition 1 over a representative phosphonate and polymer in the length of a scale squeeze treatment.

Four squeeze simulations were carried out with Composition 1 in Berea sandstone. The summary of the injection schexes (brines, volumes, permeabilities, etc.) is shown in Table 8.

were identical. This test was designed to determine conditions for optimal precipitation.

Core 12 used an alternate precipitation method. The calcium was included in the inhibitor slug and the inhibitor held in solution by lowering pH (to 4.0). The inhibitor should precipitate in the core as pH rises due to reaction of the acid with the core minerals and/or dilution. During production the lowest pH was 5.64, indicating that the acid was neutralized or diluted to a pH where precipitation should occur.

Production history results are presented in FIGS. 3–7. FIGS. 3–6 show the amount of inhibitor produced as a function of cumulative pore volumes of produced fluids. FIG. 7 presents the results in percent of initially retained inhibitor versus cumulative pore volumes of production. Originally retained inhibitor is the total axount of inhibitor injected minus the axount that exits the core during injection. The axount of inhibitor that

TABLE 8

SUMMARY OF CORE FLOOD SCALE SIMULATION STUDIES ON
BEREA SANDSTONE USING COMPOSITION 1

| | | | Saturation (% P.V.) | | | | | | | | |
|---|---|---|---|---|---|---|---|---|---|---|---|
| Core # | Pore Volumes Saturation Brine | | Connate Brine | Perm. (md.) | Water-flood Residual Oil | Perm. (md.) | Water-flood Brine | Perm. (md.) | Preflush Slug | | |
| | | | | | | | | | Brine | % P.V. | Perm. (md.) |
| 7 | 306.6 | 8% NaCl/1000 ppm Ca | 27.9 | 625 | 38.3 | 423 | 33.8 | 86.9 | 8% NaCl/ 5450 ppm Ca | 60.0 | 80.5 |
| 8 | 298.6 | " | 27.1 | 537 | 34.6 | 367 | 38.3 | 61.2 | None | — | — |
| 12 | 301.6 | " | 30.6 | 655 | 35.5 | 381 | 33.9 | 74.2 | None | — | — |
| 16 | 301.0 | " | 100 | 434 | 0 | — | — | — | None | — | — |

| Core # | Inhibitor Slug | | Perm. (md.) | amt. ret. (mg.) | amt. inj. out (%) | Postflush Slug | | Perm. (md.) | Drive | |
|---|---|---|---|---|---|---|---|---|---|---|
| | Brine | % P.V. | | | | Brine | % P.V. | | Brine | Perm. (md.) |
| 7 | 10% Comp. 1/9% NaCl | 9.9 | n.m | 2539 | 16.5 | 8% NaCl/ 5450 ppm Ca | 60.1 | n.m. | 8% CaCl/ 1000 ppm Ca | 65.6 |
| 8 | " | 10.0 | 50.9 | 2381 | 20.6 | 8% NaCl/ 5450 ppm Ca | 61.0 | n.m. | 8% CaCl/ 1000 ppm Ca | 62.6 |
| 12 | Acid** | 10.0 | 43.8 | 2130 | 22.8 | 8% NaCl/ 100 ppm Ca | 61.2 | 46.5 | 8% CaCl/ 1000 ppm Ca | 49.2 |
| 16 | 10% Comp. 1/9% NaCl | 10.0 | n.m. | 3020 | 0 | 8% NaCl/ 1000 ppm Ca | 59.1 | 349 | 8% CaCl/ 100 ppm Ca | 266 |

Core porosities averaged 23 percent while permeability to brine averaged 560 md. Permeabilities did not decrease drastically, indicating that the procedures did not plug the cores due to the inhibitor precipitation.

All cores were saturated with a brine containing 8% NaCl and 1,000 ppm Ca. In three cores waterflooded residual oil conditions were simulated. The fourth, core 16, was a test to determine the ability of Composition 1 to set into a core mainly by adsorption. No harder brine was used to set-in (precipitate) the inhibitor. Cores 7 and 8 involved a 60% P.V. (pore volumes) brine containing 5450 ppm calcium, with 8% NaCl, to precipitate the inhibitor in the core. Core 7 also had the same brine in front of the inhibitor slug. All other test parameters exits the cores during injection is generally around 20% of total injected.

The first part of the production history (to 2 P.V.) is shown in FIG. 3. Peak inhibitor production is between 65 and 75% P.V. Since a 60% P.V. postflush was used, this would indicate the axount in the inhibitor slug that was not precipitated or adsorbed. A high production peak is generally observed in lab studies and during field production from squeeze treatments. Ideally, this peak will be low, allowing more inhibitor to be produced later in the flood. The product peak is much higher (18,000 ppm) for the core where a high calcium brine is not used to precipitate the inhibitor.

Further production history shows the advantage of precipitation squeezes over adsorption only squeezes.

The concentration of the non-precipitated inhibitor drops below 10 ppm (the selected cut-off concentration) at 55 P.V., see FIG. 5, while the other tests were still producing at higher concentration at this point. The inhibitor could not be retained for long since 70% of the inhibitor was produced by 5 P.V. of production.

The core with no preflush and the acid squeeze produced about the same amount of inhibitor during the peak, see FIG. 3 and 7. The core with the pre- and postflush had the smallest peak.

Production concentrations were all identical (at 100 ppm) at 6 P.V., as FIG. 4 shows. The calcium postflush cores, on further flushing, produced at higher concentrations. The concentrations from the other two decreased rather rapidly, decreasing to below 10 ppm at 55 P.V. for the adsorption-only core and 80 P.V. from acid-squeeze core, see FIG. 5. Surprisingly, Composition 1, even when not being set-in with calcium, lasted as long as a squeeze with Composition 21 involving a calcium postflush under identical conditions. This may be due to the solubility differences of the calcium salts or to an adsorption advantage of Composition 1.

The production concentration of Composition 1 from the acid squeeze procedure probably dropped below 10 ppm so much sooner than the postflush cores because more inhibitor was permanently retained. As FIG. 7 shows, only 63 percent of originally retained inhibitor was ultimately produced from this core. Around 76 percent was returned with the postflush tests. The core with no calcium set-in produced 82 percent of injected inhibitor.

FIG. 6 shows that the cores with calcium postflushes produced inhibitor above 8 ppm for 180 P.V. The core with no preflush produced at a slightly lower concentration than the preflush test through most of the lifetime of the flushes. It produced at between 8 and 10 ppm from 110 to 180 P.V., but has the same inhibitor concentration as the other right before both concentrations start dropping rapidly toward zero. The no-preflush core could have produced at a concentration below the preflush core throughout the later stages of the flush since more was produced during the initial high concentration spike. A preflush did not extend the life of the squeeze other than in producing a higher concentration through the later stages of the flood.

Composition 1 Retention Relative to Other Inhibitors

A precipitation squeeze with Composition 1 lasted three times as long as a squeeze with the phosphonate inhibitor, Composition 21, and seven times as long as a squeeze with the polymer inhibitor Composition 18. FIG. 8 through 12 show the production histories for cores run identically, except for the inhibitor used. All runs used a calcium postflush only.

FIG. 8 shows that Composition 18 initially produces a very high concentration of inhibitor, nearly 14,000 ppm. One-half of retained inhibitor is produced within 2 P.V. of production. The inhibitor concentration then drops rapidly, even below the concentration of Composition 1. The drop continues rapidly and falls below 10 ppm concentration by 25 P.V. of production. Only 60 percent of retained inhibitor is ultimately produced, however.

The peak concentration of Composition 21 is only one-third as high as the Composition 1 peak concentration. However, the concentration of Composition 1 drops quickly. The concentration of Composition 21 only drops below that of Composition 1 at 25 P.V. of production and drops below 10 ppm at 60 P.V. of production. Composition 21 produces 72 percent of originally retained inhibitor, while Composition 1 produces a few percent more. The calcium phosphonate apparently is too soluble to be retained for a long time, relative to Composition 1, in brines with low calcium.

Calcium Pre- and Postflushes

The productions profiles of Composition 21 and Composition 1 when precipitated by calcium postflushes are similar to those where calcium preflushes as well as postflushes are used, as FIGS. 13 through 16 show. The peak productions are closer in concentration where a preflush is used, but the concentration of Composition 21 drops below 10 ppm even faster. FIG. 15 shows whereas Composition 21 reaches this concentration at 35 P.V., Composition 1 lasts 5 times as long (to 170 P.V.). Also, ultimate production of Composition 27 and Composition 1 were almost identical when preflushes were used.

The reason is not clear why Composition 1 takes an initial production spike larger than the spike from Composition 21. The calcium salt is much more insoluble so should precipitate better. It is believed that Composition 1 was selectively precipitating, that is, one or more of the four components was tolerant to calcium precipitation while one or more were very insoluble as the calcium salt. However, precipitation studies, discussed in the next section, indicate that the four components of Composition 1 have similar solubilities in their calcium forms.

Precipitation Studies

As part of another study, differing amounts of Composition 1 were added to a synthetic calcium containing brine. This brine contains 16,800 ppm $Na^+$, 2160 ppm $Ca^{+2}$, 243 ppm $Mg^{+2}$, 244 ppm $HCO_3^-$ and 161 ppm $SO_4^{-2}$. Composition 1 begins to precipitate in the brine at a concentration of 40 ppm. At differing concentrations of inhibitor—up to 100,000 ppm, the effluent was analyzed for calcium and inhibitor. Calcium was determined by EDTA titration. FIG. 17 shows the axount of precipitated calcium and Composition 1 in percent. FIGS. 18, 19 and 20 show the same information in ppm on linear, linear-log and log-log scales.

No break could be seen in the precipitation plot until large amounts of Composition 1 are added, indicating no solubility break of one component to another or that only one component is precipitating at first. The concentration of Composition 1 was determined from a standard plot. This plot will give accurate concentrations only if the components are not being separated. The axount of calcium precipitated reaches a maximum at 60,000 ppm added Composition 1 then begins to decrease, as does the axount of precipitated Composition 1. Log concentration of Composition 1 and calcium precipitated are both linear with respect to added inhibitor up to 60,000 ppm. The large axount of inhibitor could cause the product to act as a chelant for calcium, thereby decreasing the precipitated concentration of both.

FIG. 21 shows the molar ratio of calcium to active Composition 1 with increasing inhibitor. The xoles of inhibitor was calculated from an average molecular weight determined from theoretical activity and component ratio determination by $^{31}P$ NMR. The ratio approached 2:1 rather quickly. The ratio is 4 at 4000 ppm Composition 1 and between 4 and 16 down to 70 ppm. The ratio appears very high at lower amounts of Composition 1—70 at 50 ppm and 250 at 40 ppm (where precipitation commences).

This ratio assumes all components are precipitating equally. If the oligomer only is precipitating then the Ca/oligomer ratio would be right at one. The break in log-log linearity at 60,000 ppm may indicate a second component beginning to precipitate. However, $^{31}P$ NMR analysis of the effluent from the 100,000 ppm mixture indicates that the component ratios were the same as before precipitation. The standardization plots have already been done and are shown in FIG. 22. This figure also shows the large differences in determined concentrations that can be obtained if different components are being precipitated and assumed to be a certain component mixture. The concentration in FIG. 22 are as received. FIG. 23 shows standardization plots adjusted to an active basis.

A calcium carbonate inhibition study was done for products rich in the other three components of Composition 1 (besides the oligomer). A standard test was used, see Appendix 1, except that 50 mL of brine was used instead of 100 mL. The results are presented in FIG. 24. Since dissolved $CO_2$ is used, the performance with 100 mL of solution should be better than those obtained; the relative number should be the same. The solutions are compared on an actives basis, relative to Composition 1, in FIG. 25.

The results indicate that the product containing the oligomer inhibits $CaCO_3$ the best. The product high in the 2:1 adduct also has fairly good inhibition; inhibition approaches 70% at low concentrations but does not give complete inhibition as concentration increases.

One aspect of Composition is its ability to inhibit barium sulfate scale. The need for barium inhibition is becoming increasingly important at many locations, especially Alaska and many overseas locations. High temperatures are also encountered at many of these locations. Composition 21 has comparable performance in one test under one set of conditions, Table 5, but is inferior in another, Table 6.

TEST METHOD 1

Calcium Carbonate Deposition Test

Apparatus

1. Constant temperature bath (100° to 200° F.)
2. Glass test cells (4 oz. bottles with screw lid)
3. Synthetic brines
   A. 12.16 gms/L $CaCl_2.2H_2O$ 3.68 gm/L $MgCl_2.6H_2O$ 33 gm/L NaCl
   B. 7.36 gms/L $NaHCO_3$ 29.4 mg/L $Na_4SO_4$ 33 gm/L NaCl
4. Graduated cylinders 2-50 ml
5. Appropriate solutions of inhibitors to be tested
6. Pipettes: 1-0.1 ml, 1-1.0 ml and 1-10 ml
7. 125 ml Erlenmeyer flasks for each inhibitor to be tested
8. Standard EDTA solution (1 ml = 1 mg of $CaCO_3$)
9. 6 Normal sodium hydroxide
10. Ammonium purpurate indicator
11. 10 ml micro buret Procedure 1. Using the appropriate solutions of inhibitors, pipette the desired amount of inhibitor into each test cell.
2. Two controls (blanks) are set up with each test. Control contains no inhibitor.
3. Brines A and B should be saturated with $CO_2$ for thirty minutes before using.
4. Add 50 ml of Brine A and B to each test cell.
5. Cap test cells and agitate to thoroughly mix brines and chemicals.
6. Put test cell in water bath at 160° F. for 24 hours.
7. After exposure at the 160° temperature for 24 hours, the test cells are removed and allowed to cool to room temperature.
8. Pipette 1 ml of the brine from each test cell and transfer to the Erlenmeyer flask.
9. Add 50 ml of distilled water to the Erlenmeyer.
10. Add 1 ml of 6N sodium hydroxide.
11. Add a small amount of ammonium purpurate indicator and titrate with the EDTA solution. The color changes from pink to violet.
12. The amount of $CaCO_3$ retained in solution is computed by multiplying the ml of standard EDTA solution used by 1000. The results are expressed as calcium carbonate.
13. A typical scale evaluation is found below:

| Calcium Carbonate Retained in Solution (mg/L) | | | | | |
|---|---|---|---|---|---|
| Chemical | 1 ppm | 3 ppm | 5 ppm | 10 ppm | 20 ppm |
| A | 3,000 | 3,400 | 3,800 | 4,000 | 4,300 |
| B | 3,500 | 4,000 | 4,100 | 4,100 | 4,100 |
| C | 3,600 | 4,300 | 4,300 | 4,300 | 4,300 |
| Blank (after precipitation) | 2,600 mg/l as $CaCO_3$ | | | | |
| Blank (before precipitation) | 4,300 mg/l as $CaCO_3$ | | | | |

14. Test results may be recorded in percent inhibition as illustrated below.

| Test Results in Percent Inhibition | | | | | |
|---|---|---|---|---|---|
| Chemical | 1 ppm | 3 ppm | 5 ppm | 10 ppm | 20 ppm |
| A | 24 | 46 | 71 | 82 | 100 |
| B | 53 | 82 | 88 | 88 | 88 |
| C | 69 | 100 | 100 | 100 | 100 |
| Blank (after precipitation) | 2,600 mg/l as $CaCO_3$ | | | | |
| Blank (before precipitation) | 4,300 mg/l as $CaCO_3$ | | | | |

TEST METHOD 2

Calcium Sulfate Deposition Test

Apparatus

1. Constant temperature water bath (100° to 200° F.)
2. Glass test cells (4 oz. bottles with screw lids)
3. Synthetic brines
   A. Calcium brine: 1 7.5 gms/L USP NaCl 11.1 gms/L $CaCl_2.2H_2O$
   B. Sulfate brine: 7.5 gms/L UPS NaCl 10.66 gms/L $Na_2SO_4$
4. Graduated cylinders 2-50 ml
5. Appropriate solutions of inhibitors to be tested
6. Pipettes: 1-0.1 ml, 1-1.0 ml and 1-10 ml
7. 125 ml Erlenmeyer flasks for each inhibitor to be tested
8. Standard EDTA solution (1 ml = 1 mg of $CaCO_3$)
9. 6 Normal Sodium Hydroxide
10. Ammonium purpurate indicator
11. 10 ml micro buret

Procedure

1. Using the appropriate solutions of inhibitors, pipette the desired amount of inhibitor into each test cell.
2. Two controls (blanks) are set up with each test. Controls contain no inhibitor.
3. Add 50 ml of calcium chloride brine to each cell.
4. Add 50 ml of sodium sulfate brine to each cell.
5. Cap test cells and agitate to thoroughly mix brines and chemicals.
6. Put test cell in water bath at 160° F. for 24 hours.
7. After exposure at the 160° temperature for 24 hours, the test cells are removed and allowed to cool to room temperature.
8. Pipette 1 ml of the brine (pipette off the top so any calcium sulfate crystals will not be included) and transfer to the Erlenxeyer flask.
9. Add 50 ml of distilled water to the Erlenmeyer flask.
10. Add 1 ml of 6N Sodium Hydroxide.
11. Add a small axount of ammonium purpurate indicator and titrate with the standard EDTA solution. The color changes are from pink to violet.
12. The axount of calcium sulfate retained in solution is computed by multiplying the ml of standard EDTA solution used by 1000.
13. The standard API test method for calcium may be used as an alternate method.
14. A typical scale evaluation is found below:

| Chemical | CALCIUM SULFATE RETAINED IN SOLUTION AS CALCIUM CARBONATE (mg/L) | | | | |
|---|---|---|---|---|---|
| | 1 ppm | 3 ppm | 5 ppm | 10 ppm | 20 ppm |
| A | 4000 | 4000 | 4000 | 4000 | 4000 |
| B | 3000 | 3200 | 3600 | 3800 | 4000 |
| C | 3600 | 3900 | 4000 | 4000 | 4000 |
| Blank (after precipitation) | 2800 mg/l as CaCO3 | | | | |
| Blank (before precipitation) | 4000 mg/l as CaCO3 | | | | |

15. Test results may also be recorded in percent inhibition as illustrated below:

| Chemical | Test Results in Percent Inhibition | | | | |
|---|---|---|---|---|---|
| | 1 ppm | 3 ppm | 5 ppm | 10 ppm | 20 ppm |
| A | 100 | 100 | 100 | 100 | 100 |
| B | 17 | 33 | 67 | 83 | 100 |
| C | 67 | 92 | 100 | 100 | 100 |
| Blank (after precipitation) | 2800 mg/l as CaCO3 | | | | |
| Blank (before precipitation) | 4000 mg/l as CaCO3 | | | | |

TEST METHOD 3

Standard Barium Sulfate Scale Deposition Test

Procedure

Solution 1. 1% or 0.1% distilled water solutions of the chemicals being tested.
2. Brine X
   42 grams of sea salt dissolved in distilled water to make one liter of Brine X
   Sea-Salt (ASTM D-1141-52)
3. Brine Y
   25 grams of analytical grade sodium chloride and 0.0456 grams of analytical grade $BaCl_2 \cdot 2H_2O$ dissolved in distilled water to make one liter of Brine Y.
4. Brine Z
   50 grams of analytical grade $NaHCO_3$ dissolved in distilled water to make one liter of Brine Z.

Procedure

1. Saturate Brine Z for 50 minutes with $CO_2$.
2. Add chemical to be tested into a 4-ounce sample bottle.
3. Add 78 ml brine Y into the 4-ounce bottle.
4. Add 20 ml brine X into the 4-ounce bottle.
5. Add 2 ml brine Z into the 4-ounce bottle.
6. Cap and shake bottle and then allow to stand 24 hours at room temperature.
7. Filter the sample through a 0.45 millipore filter and determine the barium by atomic adsorption or Inductively Coupled Argon Plasma Spectroscopy.

Barium Analysis

Atomio Adsorption Spectroscopy Method

Barium analyses are performed on a Perkin-Elder Model 303 atomic adsorption spectophotometer employing a 5 cm slit titanium burner head and a nitrous oxide acetylene flame.

Since the barium adsorption is enhanced in high brines, the standards must be made up in a brine of the same salt content (2.5% NaCl) as the sample to be determined. Standards of 0, 5, 10, 15, 20, 30 and 50 ppm as Ba ($BaCl2 \cdot 2H2O$ in 2.5% of NaCl brine) are used for constructing a calibration curve.

Operating conditions are as follows:
Wave length: 5536A
Slit 3: 0.3 mm (4. A. Spectral Band pass)
Ba hallow cathode lamp @ 25 ma
$N_2O-C_2H_2$ flame $\frac{1}{2}''-1''$ red feather The instrument is allowed approximately five minutes warm up with the $N_2O-C_2H_2$ flame on; final wave length adjustments are then made and the 20 ppm standard is run to get the correction factor used to correct for slight changes in instrumental conditions from run and run and during a single run. In a long series of determinations, the 20 ppm standard should be run every ten to fifteen samples to correct for any drift in sensitivity during a run (i.e., the wave length can change as the very hot $N_2O-C_2H_2$ flame warms up the optical compartment).

The concentration of barium in the samples is calculated in the following manner:

$$\text{Ba in sample} = \text{Ba value from calibration curve} \times \frac{20 \text{ ppm}}{\text{Ba value from calibration curve for 20 ppm standard}}$$

Example: If 20 ppm Ba standard gave a reading of 22 ppm from the calibration curve and the sample gave 16 ppm from the curve, then the Ba concentration in the sample is:

$$Ba = 16 \times \frac{20}{22} = 16 \times .91 = 14.6$$

Ba = 15 ppm

Inductively Coupled Argon Plasma Spectroscopy Method

In the determination of barium in solutions containing high concentrations of sodium (greater than 5000 ppm) there is a decrease in the intensity of the 4934.09 emission line. In solutions containing one percent sodium this decrease is approximately twenty percent. To correct for this deviation, blanks and standards are made up in a sodium chloride solution containing the same concentration of sodium as the brine. A ten ppm barium standard is used for calibrating the instrument. This calibration is linear to one hundred ppm.

The following conditions were found to be optimum for the determination of barium on the Jarrell-Ash ICAP 9000:

Wave Length—4934.09 Angstroms
Coolant Flow—18.5 LPM
Sample Flow—0.56 LPM
Forward Power—1.1 KW
Reflected Power—<1 Watt
Observed Region—16 m.m. above the R. F. Coil Pump
 Speed—2.5 ml/min A fifteen minute warm-up time is suggested before standardization. A one minute deionized water rinse is needed between samples to prevent the nebulizer from plugging. The instrument should be restandardized every two hours to correct for variations in sample uptake rate caused by salt buildup on the torch tip.

We claim:

1. An improved squeeze treatment for preventing and removing scale from the surfaces of oil wells and the formations adjacent to the casing of these wells, said squeeze treatment being of the type wherein the injection of the flood water is stopped, a solution containing scale inhibitor is introduced under increased pressure into the wellbore penetrating the formation adjacent to the wellbore, the improvement which comprises using as the scale inhibitor a predominantly phosphinate containing composition comprising:

| Ingredients | Mole Percent - Less Than |
|---|---|
| A. Monosodium phosphinicobis - (succinic acid) | 22 |
| B. Monosodium phosphinico-succinic acid | 26 |
| C. Sodium phosphonosuccinic acid | 12 |
| D. Sodium phosphate | 5 |
| E. Sodium phosphite | 6 |
| F. Sodium hypophosphite, and | 6 |
| G. A phosphinicosuccinic acid oligomer having the probable structural formula: | |

$$\left(CH\text{---}CH\right)_m\text{---}\underset{\underset{OM}{\mid}}{\overset{\overset{O}{\|}}{P}}\text{---}\left(CH\text{---}CH\right)_n$$
$$\underset{COOM}{\mid}\ \underset{COOM}{\mid}\qquad\underset{COOM}{\mid}\ \underset{COOM}{\mid}$$

wherein G exceeds 25 mole percent, M is H, Na, K, NH$_4$, amine salts and mixtures thereof and m and n are either 0 or a small whole number with the proviso that either m or n is a small whole number and the sum of m plus n is greater than 2.

2. The improved squeeze treatment of claim 1 where G is between 35–40 mole %.

3. The improved squeeze treatment of claim 1 or 2 wherein a low or high calcium brine flush follows the introduction of the inhibitor into the formation.

4. The improved squeeze treatment of claim 3 wherein the brine flush is a high calcium brine flush.

5. The improved squeeze treatment of claim 1 or 2 wherein a low or high calcium brine flush precedes the introduction of the inhibitor into the formation.

6. The improved squeeze treatment of claim 1 or 2 wherein the scale sought to be prevented or removed contains barium.

7. An improved squeeze treatment for preventing and removing scale from the surfaces of oil wells and the formations adjacent to the casing of these wells, said squeeze treatment being of the type wherein the injection of the flood water is stopped, a solution containing scale inhibitor is introduced under increased pressure into the wellbore penetrating the formation adjacent to the wellbore, the improvement which comprises using as the scale inhibitor a predominantly phosphinate containing composition comprising:

| Ingredients | Mole Percent - Less Than |
|---|---|
| A. Monosodium phosphinicobis - (succinic acid) | 22 |
| B. Monosodium phosphinico-succinic acid | 26 |
| C. Sodium phosphonosuccinic acid | 12 |
| D. Sodium phosphate | 5 |
| E. Sodium phosphite | 6 |
| F. Sodium hypophosphite, and | 6 |
| G. A phosphinicosuccinic acid oligomer having the probable structural formula: | |

$$\left(CH\text{---}CH\right)_m\text{---}\underset{\underset{OM}{\mid}}{\overset{\overset{O}{\|}}{P}}\text{---}\left(CH\text{---}CH\right)_n$$
$$\underset{COOM}{\mid}\ \underset{COOM}{\mid}\qquad\underset{COOM}{\mid}\ \underset{COOM}{\mid}$$

wherein G exceeds 25 mole percent, M is H, Na, K, NH$_4$, amine salts mixtures thereof and m and n are either 0 or a small whole number with the proviso that either m or n is a small whole number and the sum of m plus n is greater than 2, said improved squeeze treatment further comprising the steps of:

a) introducing a low brine pad solution into the formation following the introduction of the inhibitor into the formation and then;

b) introducing a high calcium brine flush into the formation.

8. The improved squeezed treatment of claim 7 wherein G is between 35–40 mole %.

* * * * *